US011759549B2

(12) United States Patent
Alsberg

(10) Patent No.: US 11,759,549 B2
(45) Date of Patent: Sep. 19, 2023

(54) INTERPENETRATING POLYMER NETWORK HYDROGEL

(71) Applicant: CASE WESTERN RESERVE UNIVERSITY, Cleveland, OH (US)

(72) Inventor: Eben Alsberg, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 0 days.

(21) Appl. No.: 16/107,708

(22) Filed: Aug. 21, 2018

(65) Prior Publication Data

US 2019/0054211 A1    Feb. 21, 2019

Related U.S. Application Data

(60) Provisional application No. 62/548,243, filed on Aug. 21, 2017.

(51) Int. Cl.

| A61L 27/44 | (2006.01) |
|---|---|
| A61L 27/36 | (2006.01) |
| A61L 27/52 | (2006.01) |
| A61L 27/54 | (2006.01) |
| A61L 27/58 | (2006.01) |
| C08L 89/06 | (2006.01) |
| C08L 5/04 | (2006.01) |
| C08B 37/00 | (2006.01) |
| C08H 1/06 | (2006.01) |
| A61L 27/26 | (2006.01) |
| A61L 27/38 | (2006.01) |
| C08G 65/00 | (2006.01) |
| A61L 27/20 | (2006.01) |

(52) U.S. Cl.
CPC ............ *A61L 27/44* (2013.01); *A61L 27/20* (2013.01); *A61L 27/26* (2013.01); *A61L 27/3608* (2013.01); *A61L 27/3834* (2013.01); *A61L 27/52* (2013.01); *A61L 27/54* (2013.01); *A61L 27/58* (2013.01); *C08B 37/0084* (2013.01); *C08G 65/002* (2013.01); *C08H 1/06* (2013.01); *C08L 5/04* (2013.01); *C08L 89/06* (2013.01); *A61L 2300/236* (2013.01); *A61L 2300/252* (2013.01); *A61L 2300/412* (2013.01); *A61L 2300/414* (2013.01); *A61L 2400/16* (2013.01); *A61L 2430/40* (2013.01); *C08L 2205/04* (2013.01); *C08L 2312/00* (2013.01)

(58) Field of Classification Search
None
See application file for complete search history.

(56) References Cited

U.S. PATENT DOCUMENTS

| 2,536,893 A | 1/1951 | Speakman et al. |
|---|---|---|
| 5,490,978 A | 2/1996 | Spaltro et al. |
| 8,388,948 B2 | 3/2013 | Basu et al. |
| 9,370,606 B2 | 6/2016 | Nakamura et al. |
| 9,642,914 B2 | 5/2017 | Alsberg et al. |
| 2008/0226692 A1 | 9/2008 | Sato et al. |
| 2016/0008475 A1* | 1/2016 | Alsberg ............... A61K 47/00 424/93.7 |
| 2016/0279868 A1 | 9/2016 | Burdick et al. |
| 2017/0327813 A1 | 11/2017 | Cattolico et al. |

FOREIGN PATENT DOCUMENTS

WO    90/10454 A1    9/1990

OTHER PUBLICATIONS

Lee et al. (Prog Polym Sci. Jan. 2012 ; 37(1): 106-126) Alginate: properties and biomedical applications.*
Kadri et al. (RSC Adv., 2016, 6, 27879-27884) Preparation and characterization of nanofunctionalized alginate/methacrylated gelatin hybrid hydrogels.*
Applicant: Case Western Reserve University, et al.; European Patent Application No. 17879074.7, Filing Date: Dec. 11, 2017; Communication pursuant to Article 94(3) EPC; Substantive Examiner: M. Rodriguez-Palmero, Date: Jul. 20, 2020; 10 pgs.
Chelsea S. Bahney, et al., "Stem Cell-Derived Endochondral Cartilage Stimulates Bone Healing by Tissue Transformation", Journal of Bone and Mineral Research, vol. 29, No. 5, Apr. 22, 2014, pp. 1269-1282.
Chelsea S. Bahney, et al., "The Multifaceted Role of the Vasculature in Endochondral Fracture Repair", Frontiers in Endocrinology, vol. 6, Feb. 5, 2015 (Feb. 5, 2015), p. 4.
Dazai S, et al., "Leukemia inhibitory factor enhances bone formation in calvarial bone defect", The Journal of Craniofacial Surgery, Nov. 2000, vol. 11, No. 6, Nov. 2000, pp. 513-520.
Guihard P, et al., "Induction of osteogenesis in mesenchymal stem cells by activated monocytes/macrophages depends on Oncostatin M signaling", vol. 50, May 2012.
Talian Patent Office, Document No. 102011902009885A1, (Bionest Ltd), Jul. 1, 2013 (Jul. 1, 2013).
L. Yang, et al., "Hypertrophic chondrocytes can become osteoblasts and osteocytes in endochondral bone formation", Proceedings of the National Academy of Sciences, vol. 111, No. 33, Aug. 19, 2014, pp. 12097-12102.
Rachelle W. Johnson, et al., "Glycoprotein130 (Gp130)/interleukin-6 (IL-6) signalling in osteoclasts promotes bone formation in periosteal and trabecular bone", Bone, vol. 81, Aug. 7, 2015, pp. 343-351.
Rozen, et al., "Fracture repair: Modulation of fracture-callus and mechanical properties by sequential application of IL-6 following PTH 1-34 or PTH 28-48, IL-6 following PTH 1-34 or PTH 28-48", Bone, Pergamon Press., Oxford, GB, vol. 41, No. 3, Aug. 8, 2007, pp. 437-445.

(Continued)

*Primary Examiner* — Tigabu Kassa
(74) *Attorney, Agent, or Firm* — TAROLLI, SUNDHEIM, COVELL & TUMMINO LLLP

(57) ABSTRACT

An interpenetrating polymer network (IPN) structured hydrogel includes a crosslinked first natural polymer macromer with a first elasticity and an interpenetrating network of crosslinked second natural polymer macromers having a second elasticity higher than the first elasticity, the IPN structured hydrogel being cytocompatible, and, upon degradation, produce substantially non-toxic products.

11 Claims, 22 Drawing Sheets

(56) References Cited

OTHER PUBLICATIONS

Xin Zhou, et al., "Chondrocytes Transdifferentiate into Osteoblasts in Endochondral Bone during Development, Postnatal Growth and Fracture Healing in Mice", PLOS Genetics, vol. 10, No. 12, Dec. 4, 2014.
First Named Inventor: Eben Alsberg; U.S. Appl. No. 16/107,756, filed Aug. 21, 2018; NonFinal Office Action, dated Aug. 26, 2020; 16 pgs.
First Named Inventor: Eben Alsberg; U.S. Appl. No. 16/107,774, filed Aug. 21, 2018; NonFinal Office Action, dated Sep. 17, 2020; 16 pgs.
First Named Inventor: Eben Alsberg; U.S. Appl. No. 16/726,375, filed Dec. 24, 2019 NonFinal Office Action; dated Oct. 5, 2020.
Applicant: Case Western Reserve University; PCT International Application No. PCT/US19/26678; International Filing Date: Apr. 9, 2019; PCT International Search Report and Written Opinion; Authorized Officer: Lee W. Young; Date of Completion: Jun. 11, 2019; 11 pgs.
First Named Inventor: Eben Alsberg; U.S. Appl. No. 12/191,034, filed Aug. 13, 2008; NonFinal Office Action, dated Oct. 4, 2022; 28 pgs.
First Named Inventor: Eben Alsberg; U.S. Appl. No. 16/107,756, filed Aug. 21, 2018; NonFinal Office Action, dated Nov. 17, 2022; 33 pgs.
Gomez, et al. (Carbohydrate Polymers 67 (2007) 296-304) (Year: 2007).
First Named Inventor: Eben Alsberg; U.S. Appl. No. 16/044,182, filed Jul. 24, 2018; Non-Final Office Action, dated Jun. 24, 2022; 18 pgs.
First Named Inventor: Eben Alsberg; U.S. Appl. No. 16/153,138, filed Oct. 5, 2018; NonFinal Office Action, dated Aug. 12, 2022; 17 pgs.
First Named Inventor: Eben Alsberg; U.S. Appl. No. 17/544,544, filed Dec. 7, 2021; NonFinal Office Action, dated Dec. 8, 2022; 6 pgs.

* cited by examiner a b c

INTERPENETRATING POLYMER NETWORK HYDROGEL

RELATED APPLICATION

This application claims priority from U.S. Provisional Application No. 62/548,243, filed Aug. 21, 2017, the subject matter of which is incorporated herein by reference in its entirety.

GOVERNMENT FUNDING

This invention was made with government support under Grant Nos. R01AR069564, R01AR066193, and T32AR007505 awarded by The National Institutes of Health. The United States government has certain rights to the invention.

BACKGROUND

Tissue engineers aim to drive the formation of functional replacement tissues and organs, often by encapsulating cells with regenerative potential within a biomaterial matrix presenting specific signals to control their behavior. Hydrogel biomaterials are in high demand for biomedical applications, such as tissue engineering scaffolds, drug delivery vehicles and wound healing dressings, since they possess many physical and biochemical properties that are similar to natural extracellular matrix. The behavior of many cell populations can be modulated during development, homeostasis, healing processes and in vitro via exposure to mechanical stimulation in the form of compressive, tensile, shear and/or hydrostatic stress. It is for this reason that a great deal of research has been conducted focusing on understanding the role of mechanical stimulation applied to cells encapsulated in hydrogels to regulate their behaviors, such as proliferation and differentiation, and to create functional tissue engineered constructs. The application specifically of cyclic compressive stress has been shown to increase stem cell proliferation and osteogenic and chondrogenic differentiation in hydrogels. However, currently, biocompatible, biodegradable hydrogels either permanently deform and/or break under repeated compressive loading, and thus there is a critical need for highly elastic, strong hydrogels to progress this mechanostimulation strategy in the tissue engineering field.

Over the past decades, intense efforts have been devoted to the engineering of highly elastic and tough hydrogels, including microsphere composite hydrogels, nanocomposite hydrogels and interpenetrating polymer network (IPN)-structured hydrogels. Among them, IPN-structured hydrogels have attracted significant interest because of their simplicity of synthesis, impressive mechanical properties, high transparency, and their capacity to respond rapidly to external mechanical stimuli. These characteristics of IPN-structured hydrogels are desirable for investigating the role of mechanics on encapsulated cell behavior, but despite recent success in developing IPN-structured elastomeric hydrogels, it remains a great technical challenge to make them cytocompatible and biodegradable due to the use of toxic chemicals and non-biodegradable prepolymers, and the involvement of harsh reactions.

SUMMARY

Embodiments described herein relate to interpenetrating polymer network (IPN) structured hydrogels, methods of forming the hydrogels, and to their use in regenerative medicine, cell-based technologies, drug delivery, and tissue engineering applications. The IPN-structured hydrogels include a crosslinked first natural polymer macromer with a first elasticity that from a biodegradable and cytocompatible scaffold or matrix and an interpenetrating network of crosslinked second natural polymer macromer having a second elasticity higher than the first elasticity. Advantageously, the IPN-structured hydrogel exhibits highly elastic properties, cytocompatibility, biodegradability, and toughness. For example, the IPNs structured hydrogels described herein can fully recover their original thickness from large strains and long-term cyclic strain loading. The physical properties of IPN-structured hydrogels can be controllable, and their high elasticity can be preserved during degradation.

The first natural polymer macromers are crosslinked with a first agent, and the second natural polymer macromer are crosslinked with a second agent different than the first agent. In some embodiments, the first agent can crosslink the first natural polymer macromers but not the second natural polymer macromers, and the second agent can crosslink the second natural polymer macromers but not the first natural polymer macromers.

In some embodiments, the first natural polymer macromers are polysaccharides, which are optionally oxidized, such as oxidized alginates. The first natural polymer macromers can be ionically crosslinkable with the first agent.

In other embodiments, the second natural polymer macromers can include acrylated and/or methacrylated gelatin that is photocrosslinkable with the second agent.

In other embodiments, the IPN-structured hydrogel can include a plurality of cells dispersed on and/or within the hydrogel. The cells can be any cells including, for example, undifferentiated stem cells or progenitor cells with a cell lineage potential that corresponds to the desired tissue being engineered and/or differentiated cells. The cells can be unipotent, oligopotent, multipotent, or pluripotent. In some embodiments, the cells are adult stem cells. The cells can be allogeneic or autologous. In particular embodiments, the cells include mesenchymal stem cells (MSCs). The composition can contain a single cell type, such as MSCs. However, in some embodiments, the composition contains two or more different types of cells, i.e., cells of two or more different lineages. The cells can be animal cells, such as human cells.

The IPN-structured hydrogel can also include at least one bioactive agent. The bioactive agent can include, for example, at least one of BMP-2 or TGF-β.

DETAILED DESCRIPTION

Figure 1:
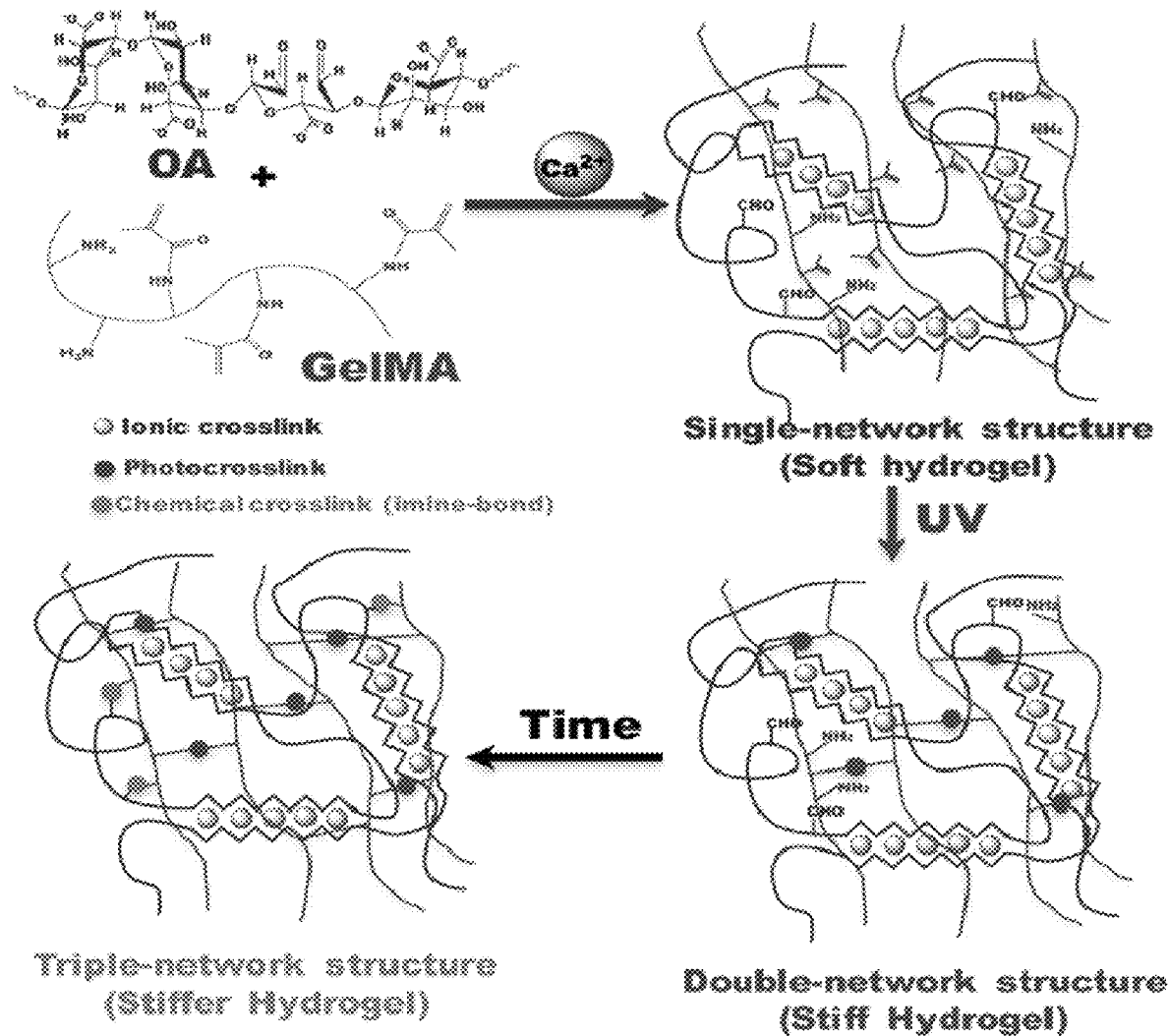
FIG. 1 illustrates a schematic showing the molecular structure and microstructure of highly elastomeric IPN-structured hybrid hydrogels formed by a triple-network in accordance with one embodiment.

Methods involving conventional molecular biology techniques are described herein. Such techniques are generally known in the art and are described in detail in methodology treatises, such as *Current Protocols in Molecular Biology*, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the present invention pertains. Commonly understood definitions of molecular biology terms can be found in, for example, Rieger et al., *Glossary of Genetics: Classical and Molecular*, 5th Ed., Springer-Verlag: New York, 1991, and Lewin, *Genes V*, Oxford University Press: New York, 1994. The definitions provided herein are to facilitate understanding of certain terms used frequently herein and are not meant to limit the scope of the present invention.

In the context of the present invention, the term "bioactive agent" can refer to any agent capable of promoting tissue growth, inhibition, formation, destruction, and/or targeting a specific disease state. Examples of bioactive agents can include, but are not limited to, chemotactic agents, various proteins (e.g., short term peptides, bone morphogenic proteins, collagen, glycoproteins, and lipoprotein), cell attachment mediators, biologically active ligands, integrin binding sequence, various growth and/or differentiation agents and fragments thereof (e.g., epidermal growth factor (EGF), hepatocyte growth factor (HGF), vascular endothelial growth factors (VEGF), fibroblast growth factors (e.g., bFGF), platelet derived growth factors (PDGF), insulin-like growth factor (e.g., IGF-I, IGF-II) and transforming growth factors (e.g., TGF-β I-III), parathyroid hormone, parathyroid hormone related peptide, bone morphogenic proteins (e.g., BMP-2, BMP-4, BMP-6, BMP-7, BMP-12, BMP-13, BMP-14), transcription factors, such as sonic hedgehog, growth differentiation factors (e.g., GDF5, GDF6, GDF8), recombinant human growth factors (e.g., MP52 and the MP-52 variant rhGDF-5), cartilage-derived morphogenic proteins (CDMP-1, CDMP-2, CDMP-3), small molecules that affect the upregulation of specific growth factors, DNA fragments, DNA plasmids, MMPs, TIMPs, interfering RNA molecules, such as siRNAs, oligonucleotides, proteoglycans, glycoproteins, glycosaminoglycans, and DNA encoding for shRNA.

As used herein, the terms "biodegradable" and "bioresorbable" may be used interchangeably and refer to the ability of a material (e.g., a natural polymer or macromer) to be fully resorbed in vivo. "Full" can mean that no significant extracellular fragments remain. The resorption process can involve elimination of the original implant material(s) through the action of body fluids, enzymes, cells, and the like.

As used herein, the term "function and/or characteristic of a cell" can refer to the modulation, growth, and/or proliferation of at least one cell, such as a progenitor cell and/or differentiated cell, the modulation of the state of differentiation of at least one cell, and/or the induction of a pathway in at least one cell, which directs the cell to grow, proliferate, and/or differentiate along a desired pathway, e.g., leading to a desired cell phenotype, cell migration, angiogenesis, apoptosis, etc.

The term "gel" includes gels and hydrogels.

As used herein, the term "macromer" can refer to any natural polymer or oligomer.

As used herein, the term "polynucleotide" can refer to oligonucleotides, nucleotides, or to a fragment of any of these, to DNA or RNA (e.g., mRNA, rRNA, siRNA, tRNA) of genomic or synthetic origin which may be single-stranded or double-stranded and may represent a sense or antisense strand, to peptide nucleic acids, or to any DNA-like or RNA-like material, natural or synthetic in origin, including, e.g., iRNA, ribonucleoproteins (e.g., iRNPs). The term can also encompass nucleic acids (i.e., oligonucleotides) containing known analogues of natural nucleotides, as well as nucleic acid-like structures with synthetic backbones.

As used herein, the term "polypeptide" can refer to an oligopeptide, peptide, polypeptide, or protein sequence, or to a fragment, portion, or subunit of any of these, and to naturally occurring or synthetic molecules. The term "polypeptide" can also include amino acids joined to each other by peptide bonds or modified peptide bonds, i.e., peptide isosteres, and may contain any type of modified amino acids. The term "polypeptide" can also include peptides and polypeptide fragments, motifs and the like, glycosylated polypeptides, and all "mimetic" and "peptidomimetic" polypeptide forms.

As used herein, the term "cell" can refer to any progenitor cell, such as totipotent stem cells, pluripotent stem cells, and multipotent stem cells, as well as any of their lineage descendant cells, including more differentiated cells. The terms "stem cell" and "progenitor cell" are used interchangeably herein. The cells can derive from embryonic, fetal, or adult tissues. Examples of progenitor cells can include totipotent stem cells, multipotent stem cells, mesenchymal stem cells (MSCs), neuronal stem cells, hematopoietic stem cells, pancreatic stem cells, cardiac stem cells, embryonic stem cells, embryonic germ cells, neural crest stem cells, kidney stem cells, hepatic stem cells, lung stem cells, hemangioblast cells, and endothelial progenitor cells. Additional exemplary progenitor cells can include de-differentiated chondrogenic cells, chondrogenic cells, cord blood stem cells, multi-potent adult progenitor cells, myogenic cells, osteogenic cells, tendogenic cells, ligamentogenic cells, adipogenic cells, and dermatogenic cells.

As used herein, the term "subject" can refer to any animal, including, but not limited to, humans and non-human animals (e.g., rodents, arthropods, insects, fish (e.g., zebrafish)), non-human primates, ovines, bovines, ruminants, lagomorphs, porcines, caprines, equines, canines, felines, aves, etc.), which is to be the recipient of a particular treatment. Typically, the terms "patient" and "subject" are used interchangeably herein in reference to a human subject.

As used herein, the term "tissue" can refer to an aggregate of cells having substantially the same function and/or form in a multicellular organism. "Tissue" is typically an aggregate of cells of the same origin, but may be an aggregate of cells of different origins. The cells can have the substantially same or substantially different function, and may be of the same or different type. "Tissue" can include, but is not limited to, an organ, a part of an organ, bone, cartilage, skin, neuron, axon, blood vessel, cornea, muscle, fascia, brain, prostate, breast, endometrium, lung, pancreas, small intestine, blood, liver, testes, ovaries, cervix, colon, stomach, esophagus, spleen, lymph node, bone marrow, kidney, peripheral blood, embryonic, or ascite tissue.

As used herein, the terms "inhibit," "silencing," and "attenuating" can refer to a measurable reduction in expression of a target mRNA (or the corresponding polypeptide or protein) as compared with the expression of the target mRNA (or the corresponding polypeptide or protein) in the absence of an interfering RNA molecule of the present invention. The reduction in expression of the target mRNA (or the corresponding polypeptide or protein) is commonly referred to as "knock-down" and is reported relative to levels present following administration or expression of a non-targeting control RNA.

As used herein, the term "population" can refer to a collection of cells, such as a collection of progenitor and/or differentiated cells.

As used herein, the term "differentiated" as it relates to the cells can refer to cells that have developed to a point where they are programmed to develop into a specific type of cell and/or lineage of cells. Similarly, "non-differentiated" or "undifferentiated" as it relates to the cells can refer to progenitor cells, i.e., cells having the capacity to develop into various types of cells within a specified lineage.

Embodiments described herein relate to interpenetrating polymer network (IPN) structured hydrogels, methods of forming the hydrogels, and to their use in regenerative medicine, cell-based technologies, drug delivery, and tissue engineering applications. The IPN-structured hydrogels include a crosslinked first natural polymer macromer with a first elasticity that from a biodegradable and cytocompatible scaffold or matrix and an interpenetrating network of crosslinked second natural polymer macromer having a second elasticity higher than the first elasticity. Advantageously, the IPN-structured hydrogel exhibits highly elastic properties, cytocompatibility, biodegradability, and toughness. For example, the IPNs structured hydrogels described herein can fully recover their original thickness from large strains and long-term cyclic strain loading. The physical properties of IPN-structured hydrogels can be controllable, and their high elasticity can be preserved during degradation.

The IPN-structured hydrogel can optionally include a plurality of cells dispersed therein and be biodegradable, and, upon degradation, produce substantially non-toxic products. Advantageously, encapsulated cells, such as hMSCs, can maintain their long-term high viability in the IPN-structured hydrogels. Moreover, mechanical stimulation of the IPN-structured hydrogel can enhance cells encapsulated in the hydrogel proliferation and differentiation.

The IPN-structured hydrogels described herein can be substantially cytocompatible (i.e., substantially non-cytotoxic) and include controllable physical properties, such as degradation rate, swelling behavior, and mechanical properties. In some embodiments, the first natural polymer macromers can be crosslinked with a first agent and the second natural polymer macromers can be crosslinked with a second agent different than the first agent. The first agent and the second agent can be selected such that the first agent can crosslink the first natural polymer macromers but not the second natural polymer macromers, and the second agent can crosslink the second natural polymer macromers but not the first natural polymer macromers.

In some embodiments, the first natural polymer macromers are polysaccharides, which are optionally oxidized so that up to about 50% of the saccharide units therein are converted to aldehyde saccharide units. Control over the degree of oxidation of the natural polymer macromers permits regulation of the gelling time used to form the hydrogel as well as the mechanical properties, which allows for tailoring of these mechanical properties depending on the clinical application.

In other embodiments, the first natural polymer macromers can include alginates, which are optionally oxidized so that up to about 50% of the saccharide units therein are converted to aldehyde saccharide units. Natural source alginates, for example, from seaweed or bacteria, are useful and can be selected to provide side chains with appropriate M (mannuronate) and G (guluronate) units for the ultimate use of the polymer. Alginate materials can be selected with high guluronate content since the guluronate units, as opposed to the mannuronate units, more readily provide sites for oxidation and crosslinking. Isolation of alginate chains from natural sources can be conducted by conventional methods. See Biomaterials: Novel Materials from Biological Sources, ed. Byrum, Alginates chapter (ed. Sutherland), p. 309-331 (1991). Alternatively, synthetically prepared alginates having a selected M and G unit proportion and distribution prepared by synthetic routes, such as those analogous to methods known in the art, can be used. Further, either natural or synthetic source alginates may be modified to provide M and G units with a modified structure. The M and/or G units may also be modified, for example, with polyalkylene oxide units of varied molecular weight such as shown for modification of polysaccharides in U.S. Pat. No. 5,490,978 with other alcohols, such as glycols. Such modification generally will make the polymer more soluble, which generally will result in a less viscous material. Such modifying groups can also enhance the stability of the polymer. Further, modification to provide alkali resistance, for example, as shown by U.S. Pat. No. 2,536,893, can be conducted.

The oxidation of the first natural polymer macromers (e.g., alginate macromers) can be performed using a periodate oxidation agent, such as sodium periodate, to provide at least some of the saccharide units of the natural polymer macromer with aldehyde groups. The degree of oxidation is controllable by the mole equivalent of oxidation agent, e.g., periodate, to saccharide unit. For example, using sodium periodate in an equivalent % of from 2% to 100%, preferably 1% to 50%, a resulting degree of oxidation, i.e., % if saccharide units converted to aldehyde saccharide units, from about 2% to 50% can be obtained. The aldehyde groups provide functional sites for crosslinking and for bonding tissue, cells, prosthetics, grafts, and other material that is desired to be adhered. Further, oxidation of the first natural polymer macromer facilitates their degradation in vivo, even if they are not lowered in molecular weight. Thus, high molecular weight alginates, e.g., of up to 300,000 daltons, may be degradeable in vivo, when sufficiently oxidized, i.e., preferably at least 5% of the saccharide units are oxidized.

In some embodiments, the first natural polymer macromers can be ionically crosslinked and/or chemically crosslinked with an ionic crosslinker to form a hydrogel. For example, gluronic acids of different alginate polymer macromers can form ionic crosslinks with $Ca^{2+}$ provided by an aqueous solution of $CaCl_2$ resulting in an ionic crosslink network. The extent of crosslinking can be controlled by the concentration of $CaCl_2$. The higher concentration can correspond to a higher extent of crosslinking. The extent of crosslinking alters the mechanical properties of the hydrogel and can be controlled as desired for the particular application. In general, a higher degree of crosslinking results in a stiffer gel.

The second natural polymer macromers used to form the IPN can include crosslinkable natural polymer macromers that are different than the first polymer macromers and include a functional group (e.g., an acrylate group and/or methacrylate group) that can be crosslinked by the second agent, which is different than the first agent. Advantageously, the crosslinked second polymer macromers should have an elasticity greater the crosslinked first natural polymer macromers to enhance the elasticity of hydrogel.

In some embodiments, a crosslinked second natural polymer macromer that has an elasticity greater than the crosslinked first natural polymer macromer can include an acrylated and/or methacrylated gelatin. The second natural polymer macromer (e.g., gelatin) can be acrylated and/or methacrylated by reacting an acryl group and/or methacryl with a second natural polymer macromer (e.g., gelatin). For example, bovine type-B gelatin can be dissolved in a phosphate buffered solution and then reacted with methacrylic anhydride to provide a plurality of methacrylate groups on the gelatin.

The degree of acrylation and/or methacrylation can be controlled to control the degree of subsequent crosslinking of the acrylate and methacrylates as well as the mechanical properties, and biodegradation rate of the composition. The degree of acrylation or methacrylation can be about 1% to about 99%, although this ratio can vary more or less depending on the end use of the composition.

In some embodiments, the second agent can crosslink acrylate and/or methacrylate groups of the acrylated or methacrylated natural polymer macromer to form a plurality of second crosslinking networks. The second crosslinking networks formed by crosslinking the acrylate groups or methacrylate groups of the acrylated and/or methacrylated natural polymer macromer can enhance mechanical properties, such as elasticity, to the hydrogel.

In some embodiments, the acrylate or methacrylate groups of the acrylated and/or methacrylated second natural polymer macromer can be crosslinked by photocrosslinking using UV light in the presence of photoinitiators. For example, acrylated and/or methacrylated natural polymer macromers can be photocrosslinked in an appropriate amount of $diH_2O$ or aqueous media (e.g., PBS) containing a desired amount of a photoinitiator.

The photoinitiator can include any photo-initiator that can initiate or induce polymerization of the acrylate or methacrylate macromer. Examples of the photoinitiator can include camphorquinone, benzoin methyl ether, 2-hydroxy-2-methyl-1-phenyl-1-propanone, diphenyl(2,4,6-trimethylbenzoyl)phosphine oxide, benzoin ethyl ether, benzophenone, 9,10-anthraquinone, ethyl-4-N,N-dimethylaminobenzoate, diphenyliodonium chloride and derivatives thereof.

The acrylated and/or methacrylated natural polymer macromers can be exposed to a light source at a wavelength and for a time to promote crosslinking of the acrylate and/or methacrylate groups of the macromers and form the photocrosslinked IPN of the second natural polymer macromers.

By way of example, as illustrated in FIG. 1, the IPN-structured hydrogel can be formed, for example, by mixing oxidized alginate macromers (e.g., 2.5 w/v %) and methacrylated gelatin macromers (e.g., 20 w/v %) with a photoinitiator (e.g., 2-Hydroxy-4'-(2-hydroxyethoxy)-2-methylpropiophenone, 0.05 w/v %, Sigma). The oxidized aginate macromer can then be ionically crosslinked with a calcium solution to form a hydrogel that includes an alginate matrix or scaffold with a plurality of gelatin macromers dispersed in the scaffold. The methacrylated gelatin macromers in the hydrogel scaffold can then photocrosslinked with UV light (e.g., 320-500 nm, EXFO Omnicure® S 1000-1B, Lumen Dynamics Group) at ~20 mW/cm$^2$ for 5 min to form IPN-structured hydrogels. Mixing the two macromers together also results in imine-bond formation via Schiff base reaction between the aldehyde groups of the oxidized and the amine groups of the methacrylated gelatin.

In some embodiment, the IPN-structured hydrogel can include a plurality of cells dispersed on and/or within the hydrogel. The cells provided in the hydrogel can be autologous, xenogeneic, allogeneic, and/or syngeneic. Where the cells are not autologous, it may be desirable to administer immunosuppressive agents in order to minimize immunorejection. The cells employed may be primary cells, expanded cells, or cell lines, and may be dividing or non-dividing cells. Cells may be expanded ex vivo prior to introduction into or onto the hydrogel. For example, autologous cells can be expanded in this manner if a sufficient number of viable cells cannot be harvested from the host subject. Alternatively or additionally, the cells may be pieces of tissue, including tissue that has some internal structure. The cells may be primary tissue explants and preparations thereof, cell lines (including transformed cells), or host cells.

Generally, cells can be introduced into the IPN-structured hydrogels in vitro, although in vivo seeding approaches can optionally or additionally be employed. Cells may be mixed with the macromers used to form the IPN-structured hydrogels and cultured in an adequate growth (or storage) medium to ensure cell viability. If the IPN-structured hydrogel is to be implanted for use in vivo after in vitro seeding, for example, sufficient growth medium may be supplied to ensure cell viability during in vitro culture prior to in vivo application. Once the IPN-structured hydrogels have been implanted, the nutritional requirements of the cells can be met by the circulating fluids of the host subject.

Any available method may be employed to introduce the cells into the IPN-structured hydrogels. For example, cells may be injected into the IPN-structured hydrogels (e.g., in combination with growth medium) or may be introduced by other means, such as pressure, vacuum, osmosis, or manual mixing. Alternatively or additionally, cells may be layered on the IPN-structured hydrogels, or the IPN-structured hydrogels may be dipped into a cell suspension and allowed to remain there under conditions and for a time sufficient for the cells to incorporate within or attach to the IPN-structured hydrogel. Generally, it is desirable to avoid excessive manual manipulation of the cells in order to minimize cell death during the impregnation procedure. For example, in some situations it may not be desirable to manually mix or knead the cells with the IPN-structured hydrogels; however, such an approach may be useful in those cases in which a sufficient number of cells will survive the procedure. Cells can also be introduced into the IPN-structured hydrogels in vivo simply by placing the IPN-structured hydrogel in the subject adjacent a source of desired cells.

As those of ordinary skill in the art will appreciate, the number of cells to be introduced into the IPN-structured hydrogels will vary based on the intended application of the hydrogel and on the type of cell used. Where dividing autologous cells are being introduced by injection or mixing into the hydrogel, for example, a lower number of cells can be used. Alternatively, where non-dividing cells are being introduced by injection or mixing into the hydrogel, a larger number of cells may be required. It should also be appreciated that the IPN-structured hydrogel can be in either a hydrated or lyophilized state prior to the addition of cells. For example, the IPN-structured hydrogel can be in a lyophilized state before the addition of cells is done to re-hydrate and populate the scaffold with cells.

In other embodiments, the IPN-structured hydrogels can include at least one attachment molecule to facilitate attachment of at least one cell thereto. The attachment molecule can include a polypeptide or small molecule, for example, and may be chemically immobilized onto the IPN-structured hydrogel to facilitate cell attachment. Examples of attachment molecules can include fibronectin or a portion thereof, collagen or a portion thereof, polypeptides or proteins containing a peptide attachment sequence (e.g., arginine-glycine-aspartate sequence) (or other attachment sequence), enzymatically degradable peptide linkages, cell adhesion ligands, growth factors, degradable amino acid sequences, and/or protein-sequestering peptide sequences.

In other embodiments, the IPN-structured hydrogel can include at least one bioactive agent. The at least one bioactive agent can include any agent capable of modulating a function and/or characteristic of a cell that is dispersed on or within the IPN-structured hydrogel. Alternatively or additionally, the bioactive agent may be capable of modulating a function and/or characteristic of an endogenous cell surrounding the IPN-structured hydrogel implanted in a tissue defect, for example, and guide the cell into the defect.

Examples of bioactive agents include chemotactic agents, various proteins (e.g., short term peptides, bone morphogenic proteins, collagen, glycoproteins, and lipoprotein), cell attachment mediators, biologically active ligands, integrin binding sequence, various growth and/or differentiation agents and fragments thereof (e.g., EGF), HGF, VEGF, fibroblast growth factors (e.g., bFGF), PDGF, insulin-like growth factor (e.g., IGF-I, IGF-II) and transforming growth factors (e.g., TGF-β I-III), parathyroid hormone, parathyroid hormone related peptide, bone morphogenic proteins (e.g., BMP-2, BMP-4, BMP-6, BMP-7, BMP-12, BMP-13, BMP-14), sonic hedgehog, growth differentiation factors (e.g., GDF5, GDF6, GDF8), recombinant human growth factors (e.g., MP-52 and the MP-52 variant rhGDF-5), cartilage-derived morphogenic proteins (CDMP-1, CDMP-2, CDMP-3), small molecules that affect the upregulation of specific growth factors, polynucleotides, DNA fragments, DNA plasmids, MMPs, TIMPs, interfering RNA molecules, such as siRNAs, DNA encoding for an shRNA of interest, oligonucleotides, proteoglycans, glycoproteins, and glycosaminoglycans.

The IPN-structured hydrogel can be used in a variety of biomedical applications, including tissue engineering, drug delivery applications, and regenerative medicine. In one example, the IPN-structured hydrogel can be used to promote tissue growth in a subject. One step of the method can include identifying a target site. The target site can comprise a tissue defect (e.g., cartilage and/or bone defect) in which promotion of new tissue (e.g., cartilage and/or bone) is desired. The target site can also comprise a diseased location (e.g., tumor). Methods for identifying tissue defects and disease locations are known in the art and can include, for example, various imaging modalities, such as CT, MRI, and X-ray.

The tissue defect can include a defect caused by the destruction of bone or cartilage. For example, one type of cartilage defect can include a joint surface defect. Joint surface defects can be the result of a physical injury to one or more joints or, alternatively, a result of genetic or environmental factors. Most frequently, but not exclusively, such a defect will occur in the knee and will be caused by trauma, ligamentous instability, malalignment of the extremity, meniscectomy, failed aci or mosaicplasty procedures, primary osteochondritis dessecans, osteoarthritis (early osteoarthritis or unicompartimental osteochondral defects), or tissue removal (e.g., due to cancer). Examples of bone defects can include any structural and/or functional skeletal abnormalities. Non-limiting examples of bone defects can include those associated with vertebral body or disc injury/destruction, spinal fusion, injured meniscus, avascular necrosis, cranio-facial repair/reconstruction (including dental repair/reconstruction), osteoarthritis, osteosclerosis, osteoporosis, implant fixation, trauma, and other inheritable or acquired bone disorders and diseases.

Tissue defects can also include cartilage defects. Where a tissue defect comprises a cartilage defect, the cartilage defect may also be referred to as an osteochondral defect when there is damage to articular cartilage and underlying (subchondral) bone. Usually, osteochondral defects appear on specific weight-bearing spots at the ends of the thighbone, shinbone, and the back of the kneecap. Cartilage defects in the context of the present invention should also be understood to comprise those conditions where surgical repair of cartilage is required, such as cosmetic surgery (e.g., nose, ear). Thus, cartilage defects can occur anywhere in the body where cartilage formation is disrupted, where cartilage is damaged or non-existent due to a genetic defect, where cartilage is important for the structure or functioning of an organ (e.g., structures such as menisci, the ear, the nose, the larynx, the trachea, the bronchi, structures of the heart valves, part of the costae, synchondroses, enthuses, etc.), and/or where cartilage is removed due to cancer, for example.

After identifying a target site, such as a cranio-facial cartilage defect of the nose, the IPN-structured hydrogel can be administered to the target site. The hydrogel can be prepared by mixing a plurality of cells, such as chondrocytes, with a plurality of oxidized alginate macromers, acrylated and/or methacrylated gelatin macromers, and a photoinitiator to form a solution. Chondrocytes may be obtained from a host subject and then expanded to a desired density ex vivo. The oxidized alginate macromers in solution can then be ionically crosslinked (e.g., $Ca^{2+}$ ions) and the acrylated and/or methacrylated macromers can be photocrosslinked.

Next, the IPN-structured hydrogel may be loaded into a syringe or other similar device and injected or implanted into the tissue defect. Upon injection or implantation into the tissue defect, the hydrogel be formed into the shape of the tissue defect using tactile means.

After implanting the IPN-structured hydrogel into the subject, the chondrocytes can begin to migrate from the hydrogel into the tissue defect, express growth and/or differentiation factors, and/or promote chondroprogenitor cell expansion and differentiation.

Advantageously, the IPN-structured hydrogel can fully recover its shape (e.g., thickness) from large strains and long-term cyclic strain loading. The physical properties of IPN-structured hydrogels can be controllable, and its high elasticity can be substantially preserved or maintained during degradation when, for example, implanted in a subjected in a subject in need thereof. Moreover, cells, such as hMSCs, encapsulated in the hydrogel can maintain long-term high viability.

The following example is for the purpose of illustration only and is not intended to limit the scope of the claims, which are appended hereto.

Example

This example describes the engineering of IPN-structured hybrid hydrogels, which exhibited highly elastic properties, cytocompatibility, biodegradability and toughness, based on an ionically crosslinked alginate and photocrosslinked gelatin. The effect of alginate oxidation degree on IPN-structured hybrid hydrogel's physical properties, such as mechanical properties, swelling and biodegradation, was evaluated. Additionally, it was determined whether mechanical stimulation could affect the behavior of encapsulated stem cell, such as proliferation and differentiation.

Methods

Preparation of Oxidized Alginate (OA) and Methacrylated Gelatin (GelMA)

The OA was prepared by reacting sodium alginate (ALG, Protanal LF 20/40, 196,000 g/mol, FMC Biopolymer) with sodium periodate (Sigma) using a previously described method. Briefly, sodium alginate (10 g) was dissolved in ultrapure deionized water ($diH_2O$, 900 ml) overnight. Sodium periodate (217 mg, 543 and 1085 mg) was dissolved in 100 ml $diH_2O$ and added to separate alginate solutions to achieve different degrees of theoretical alginate oxidation (2, 5 and 10%, respectively) under stirring in the dark at room temperature (RT) for 24 hrs. The OA was purified by dialysis against $diH_2O$ (MWCO 3500; Spectrum Laboratories Inc.) for 3 days, treated with activated charcoal (0.5 mg/100 ml, 50-200 mesh, Fisher) for 30 min, filtered (0.22 μm filter) and lyophilized. The actual oxidation (Table S 1) was determined by using the Amplite™ Colorimetric Aldehyde Quantitation Kit (AAT Bioquest Inc.) according to the manufacturer's instructions.

The GelMA was synthesized by reaction of type-B gelatin with methacrylic anhydride using a previously described method. Briefly, bovine type-B gelatin (10 g, Sigma) was dissolved in 100 mL Dulbecco's phosphate buffered saline (PBS, Gibco) at 60° C. and stirred until fully dissolved. Methacrylic anhydride (10 mL, purity ≥92%, Sigma) was added at a rate of 0.5 mL/min to the gelatin solution under vigorous stirring at 50° C., and the reaction was maintained in the dark at RT for 3 hrs. The reaction mixture was precipitated into excess acetone, dried in fume hood and rehydrated to a 10 w/v % solution in $diH_2O$. The GelMA was purified by dialysis against $diH_2O$ (MWCO 12-14 kDa) for 7 days at 40° C. to remove salts, unreacted methacrylic anhydride and byproducts, filtered (0.22 μm filter) and lyophilized. The actual extent of GelMA methacrylation (Table 1) was calculated from the $^1$H-NMR spectra.

TABLE 1

Actual oxidation (%) of OAs and methacrylation (%) of GelMA

| Code | Theoretical oxidation[a] (%) | Theoretical methacrylation (%) | Actual oxidation[b] (%) | Actual methacrylation[c] (%) |
|---|---|---|---|---|
| OA-2 | 2 | — | 1.5 ± 0.2 | — |
| OA-5 | 5 | — | 4.2 ± 0.5 | — |
| OA-10 | 10 | — | 8.5 ± 0.3 | — |
| GelMA | — | — | — | 99.2 |

[a]Theoretical oxidation of uronic acid units of alginate was calculated based on the mass of alginate in 1 w/v % solution and the molecular weight of the repeat unit ($M_0$ = 198).
[b]Actual alginate oxidation was determined by using the Amplite Colorimetric Aldehyde Quantitation Kit (AAT Bioquest Inc.) according to the manufacturer's instructions.
[c]Actual methacrylation of GelMA was calculated from $^1$H-NMR data.

Preparation of IPN-Structured OA/GelMA Hydrogels

OAs (2.5 w/v %) and GelMA (20 w/v %) were dissolved separately in DMEM (Sigma) with a photoinitiator (2-Hydroxy-4'-(2-hydroxyethoxy)-2-methylpropiophenone, 0.05 w/v %, Sigma) at pH 7.4. OA (0.5 ml) and GelMA (0.5 ml) solutions were loaded separately into two 1-ml syringes, and then 22.3 μl calcium sulfate slurry ($CaSO_4.2H_2O$, 0.21 g/ml) was added into the GelMA syringe. After the two syringes were connected together with a female-female luer lock coupler (Value Plastics), the two solutions were mixed, immediately placed between quartz (top) and glass (bottom) plates separated by 0.75 mm spacers, allowed to gel for 30 min at RT, and then photocrosslinked with UV light (320-500 nm, EXFO Omnicure® S 1000-1B, Lumen Dynamics Group) at ~20 mW/cm$^2$ for 5 min to form IPN-structured hydrogels. The physical properties of the IPN-structured hydrogels were evaluated.

To determine the extent of the crosslinking between the OAs and GelMA and to determine the completeness of GelMA photocrosslinking, OAs (2.5 w/v %) and GelMA (20 w/v %) were dissolved in $D_2O$ (Sigma) with 0.05% w/v photoinitiator. OA (0.5 ml) and GelMA (0.5 ml) solutions were loaded separately into two 1-ml syringes, and then 22.3 μl calcium sulfate slurry ($CaSO_4.2H_2O$, 0.21 g/ml) was added into the GelMA syringe. After the two syringes were connected together with a female-female luer lock coupler (Value Plastics), the two solutions were mixed, placed in an NMR tube, allowed to gel for 30 min at RT, and then photocrosslinked as described above. The $^1$H-NMR spectra of the hydrogels were recorded on an NMR spectrometer (Varian Inova, Varian Inc, 600 MHz) using 3-(trimethylsilyl) propionic-2,2,3,3,-$d_4$ acid (Sigma) as an internal standard.

Characterization of Hydrogel Homogeneity

Images of IPN-structured hybrid hydrogels formed with fluorescently labeled components can demonstrate the extent of homogeneous hydrogel formation. Therefore, the alginates and GelMA were labeled with different fluorescent dyes as previously described to evaluate the homogeneity of hydrogels. OA-2 (100 mg) was dissolved in 10 ml MES buffer (50 mM MES, 0.5 M NaCl, and pH 6.5). NHS (58 mg) and EDC (194 mg) (molar ratio of NHS:EDC=1:2) were added to the OA-2 solution to activate the carboxylic acid groups of the OA-2. After 5 min, a blue fluorescent dye (0.1 mg, CF™350 hydrazide, Biotium) was added to the OA-2 solution, and the reaction was maintained in the dark at RT for 24 hrs. GelMA (1 g) was dissolved in 100 ml MES buffer (50 mM MES, 0.5 M NaCl, and pH 6.5), a red fluorescent dye (0.82 mg, CF™633 succinimidyl ester, Biotium) was added to the GelMA solution, and the reaction was maintained in the dark at RT for 24 hrs. The macromers were precipitated in excess acetone, dried in a fume hood, and rehydrated to 1% w/v solutions in di$H_2O$ for further purification. The fluorescently labeled OA-2 and GelMA were purified by dialysis against di$H_2O$ (MWCO 12-14 k Da; Spectrum Laboratories Inc.) for 3 days, filtered (0.22 μm filter) and lyophilized. OA-5 and ALG were also labeled with the blue fluorescent dye as described above. The IPN-structured hybrid hydrogels were prepared as described above and imaged using a fluorescence microscope (ECLIPSE TE 300, Nikon) equipped with a digital camera (Retiga-SRV, QImaging).

Mechanical Testing

Unconfined cyclic compression testing (5 cycles) of IPN-structured elastomeric hydrogels (3 mm diameter and 0.8 mm height) was performed using a constant crosshead speed of 1%/sec on a mechanical testing machine (225 lbs Actuator, TestResources) equipped with a 5 N load cell under constant strain (50% compressive strain) and increased strain of 10% from 10% to 50% with each successive cycle. The compressive moduli of IPN-structured hydrogels were determined from the slope of stress vs. strain plots, and limited to the first 5% of strain. To evaluate the fatigue resistance of IPN-structured hydrogels against compressive loading, the hydrogels were cyclically compressed with 10% compressive strain at a frequency of 0.5 Hz for 20000 cycles.

Cyclic tensile testing was performed using a Rheometerics Solid Analyzer (RSAII, Rheometrics Inc.) equipped with a 10 N load cell. The IPN-structured elastomeric hydrogels were prepared as described in the Experimental Section and cut into rectangular pieces with dimensions of 20×10 mm. Samples were attached to a plastic backing using cyanoacrylate glue (Kraze Glue®, Elmeris Products Inc.) with a 10 mm gauge length. After 30 min incubation in a humidity chamber, the plastic backings were loaded into the clamps of the mechanical tester and cyclic tensile tests were performed on specimens at room temperature using a constant strain rate of 4%/sec (2 cycles).

Evaluation of Physical Property Changes During Degradation

IPN-structured hydrogels were prepared. Hydrogel disks were created using a 10 mm diameter biopsy punch. The IPN-structured hydrogel disks were lyophilized and dry weights ($W_i$) were measured. Dried hydrogel samples were immersed in 10 ml of DMEM and incubated at 37° C., and DMEM was replaced every week. At predetermined time points, samples were removed, rinsed with DMEM, and the swollen ($W_s$) hydrogel sample weights were measured. The swelling ratio (Q) was calculated by $Q=W_s/W_i$ (N=3 for each time point). After weighing the swollen hydrogel samples, the samples were lyophilized and weighed ($W_d$). The percent mass loss was calculated by $(W_i-W_d)/W_i\times 100$ (N=3 for each time point).

At predetermined time points, the swollen IPN-structured hydrogel disks were punched once again using a 3 mm diameter biopsy punch, and the thickness was measured. To evaluate the elastic behavior of the IPN-structured hydrogels during degradation, unconfined cyclic compression test (2 cycles) of IPN-structured hydrogels was performed using a constant crosshead speed of 1%/sec on a mechanical testing machine (225 lbs Actuator) equipped with a 5 N load cell under 50% strain. Compressive moduli of IPN-structured hydrogels were determined from the slope of stress vs. strain plots, and limited to the first 5% of strain.

Encapsulation of hMSCs to Examine Cytocompatibiity and Cell Growth

To isolate hMSCs, bone marrow aspirates were obtained from the posterior iliac crest of a healthy twenty three-year old male donor under a protocol approved by the University Hospitals of Cleveland Institutional Review Board and processed as previously described. Briefly, the aspirates were washed with growth medium comprised of low-glucose Dulbecco's Modified Eagle's Medium (DMEM-LG, Sigma) with 10% prescreened fetal bovine serum (FBS, Gibco). Mononuclear cells were isolated by centrifugation in a Percoll (Sigma) density gradient and the isolated cells were plated at $1.8\times 10^5$ cells/$cm^2$ in DMEM-LG containing 10% FBS and 1% penicillin/streptomycin (P/S, Thermo Fisher Scientific) in an incubator at 37° C. and 5% $CO_2$. After 4 days of incubation, non-adherent cells were removed and adherent cell were maintained in DMEM-LG containing 10% FBS and 1% P/S with media changes every 3 days. After 14 days of culture, the cells were passaged at a density of $5\times 10^3$ cells/$cm^2$.

ALG or OAs (2.5 w/v %) and GelMA (20 w/v %) were dissolved separately in DMEM with a photoinitiator (2-Hydroxy-4'-(2-hydroxyethoxy)-2-methylpropiophenone, 0.05 w/v %, Sigma) at pH 7.4, and then hMSCs (passage number 3, $2\times 10^6$ cells/ml) were suspended in ALG or OAs (0.5 ml). After ALG or OAs and GelMA (0.5 ml) solutions were loaded separately into two 1-ml syringes, 22.3 μl calcium sulfate slurry ($CaSO_4.2H_2O$, 0.21 g/ml) was added into the GelMA syringe. After the two syringes were connected together with a female-female luer lock coupler (Value Plastics), the two solutions were mixed, immediately placed between quartz (top) and glass (bottom) plates separated by 0.75 mm spacers, allowed to gel for 30 min at RT, and then photocrosslinked with UV light (320-500 NM, EXFO Omnicure® S 1000-1B, Lumen Dyanmics Group) at ~20 mW/$cm^2$ for 5 min to form hydrogel-cell constructs. IPN-structured elastomeric hybrid hydrogel-construct disks were created using an 8 mm diameter biopsy punch, placed in wells of 24-well tissue culture plates with 1 ml DMEM containing 10% FBS and 1% P/S and cultured in a humidified incubator at 37° C. with 5% $CO_2$.

The viability of encapsulated hMSCs in the IPN-structured hydrogels was investigated using a Live/Dead assay comprised of fluorescein diacetate [FDA, 1.5 mg/ml in dimethyl sulfoxide (Research Organic Inc.), Sigma] and ethidium bromide (EB, 1 mg/ml in PBS, Thermo Fisher Scientific). The staining solution was freshly prepared by mixing 1 ml FDA solution and 0.5 ml EB solution with 0.3 ml PBS (pH 8). At predetermined time points, 20 μl of staining solution was added into each well and incubated for 3-5 min at room temperature, and then stained hydrogel-cell constructs were imaged using a fluorescence microscope (ECLIPSE TE 300) equipped with a digital camera (Retiga-SRV).

hMSC Osteogenesis Under Mechanical Stimulation

To evaluate the effect of mechanical stimulation on the osteogenic differentiation of encapsulated hMSC, OAs (2.5 w/v %) and GelMA (20 w/v %) were dissolved separately in DMEM with a photoinitiator, and then hMSCs (passage number 3, $2 \times 10^6$ cells/ml) were suspended in OA and GelMA solutions. hMSC suspended OA (0.5 ml) and GelMA (0.5 ml) solutions were loaded separately into two 1-ml syringes, and then 22.3 µl calcium sulfate slurry was added into the GelMA syringe. After the two syringes were connected together with a female-female luer lock coupler, the two solutions were mixed, immediately placed between quartz (top) and glass (bottom) plates separated by 0.4 mm spacers, allowed to gel for 30 min at RT, and then photocrosslinked with UV light to form IPN-structured hydrogels as described above. hMSC-laden hydrogel-cell construct disks were created using an 10 mm diameter biopsy punch and placed in wells of 24-well tissue culture plates with 0.5 ml osteogenic media [10 mM β-glycerophosphate (Cal-Biochem), 50 µM ascorbic acid (Wako), and 100 nM dexamethasone (MP Biomedicals)] containing 10% fetal bovine serum (FBS, Sigma) and 1% penicillin/streptomycin (P/S, Thermo Fisher Scientific) with media changes every 3 days. The hydrogel constructs were subjected to strain controlled, unconfined, dynamic mechanical compression using a BOSE bioreactor (ElectroForce BioDynamic test instrument, Bose, equipped with a 200 N load cell. Compressive mechanical stimulation was performed using a sine wave with a frequency of 0.5 Hz at 10% strain for 1 hr/day during the entire culture period. To determine whether osteogenic differentiation of hMSCs cultured in IPN-structured elastomeric hybrid hydrogels could be enhanced by mechanical stimulation in vitro, at predetermined time points, each hydrogel-cell construct was removed from the 24-well plates, put in 1 ml ALP lysis buffer (CelLytic™ M, Sigma) and homogenized at 35,000 rpm for 30 s using a TH homogenizer (Omni International). The homogenized solutions were centrifuged at 500 g with a Sorvall Legent RT Plus Centrifuge (Thermo Fisher Scientific). For ALP measurement, supernatant (100 µl) was treated with p-nitrophenylphosphate ALP substrate (pNPP, 100 µl, Sigma) at 37° C. for 30 min, and then 0.1 N NaOH (50 µl) was added to stop the reaction. The absorbance was measured at 405 nm using a plate reader (VersaMax, Molecular Devices) (N=4). DNA content in supernatant (100 µl) was measured using a Picogreen assay kit (Invitrogen) according to the manufacturer's instructions. Fluorescence intensity of the dye-conjugated DNA solution was measured using a fluorescence plate reader (FMAX, Molecular Devices) set at 485 nm excitation and 538 nm emission (N=4). After an equal volume of 1.2 N HCl was added into each lysate solution, the mixed solutions were centrifuged at 500 g with a Sorvall Legent RT Plus Centrifuge. Calcium content of the encapsulated hMSCs was quantified using a calcium assay kit (Pointe Scientific) according to the manufacturer's instructions. Supernatant (4 µl) was mixed with a color and buffer reagent mixture (250 µl) and the absorbance was read at 570 nm on a microplate reader (VersaMax) (N=4). All ALP and calcium content measurements were normalized to DNA content. To visualize the calcium deposition in the bulk hydrogel disks, they were fixed with 4% paraformaldehyde for 40 min, stained with Alizarin Red S (2 w/v %, pH 4.2; Sigma) for 5 min, and imaged using a digital camera (iPhone 5, Apple). To further evaluate the calcium deposition in the hydrogels, unstained fixed hydrogel-cell constructs were embedded in paraffin, sectioned at a thickness of 10 am, stained with Alizarin Red S, and then imaged using a microscope (Leitz Laborlux S, Leica) equipped with a digital camera (Coolpix 995, Nikon).

Results and Discussion

Figure 5A:
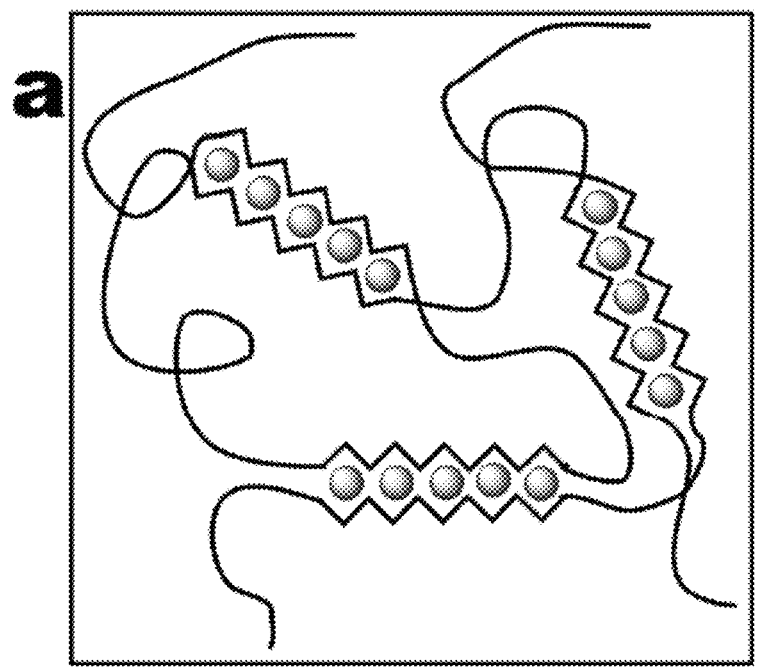
FIGS. 5(A-F) illustrate schematics showing the three types of crosslinking in the alginate-GelMA system. A) and D) show a calcium crosslinked OA hydrogel. B) and E) depict the covalent crosslinks of a UV photocrosslinked GelMA hydrogel. C) and F) exhibit the three types of polymer networks present in an OA-GelMA IPN-structured elastomeric hybrid hydrogel.
Figure 5B:
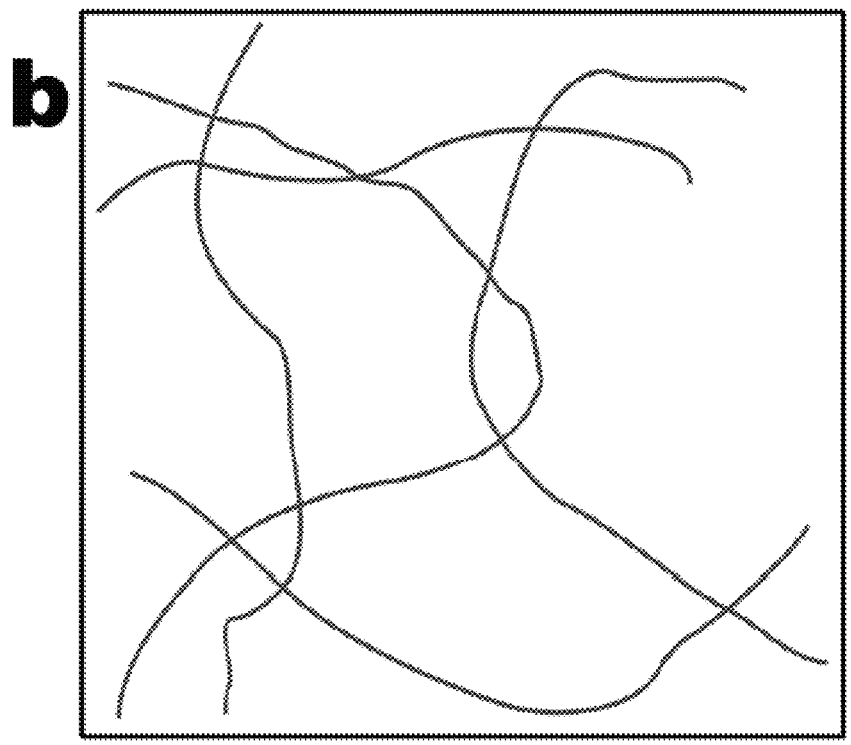
Figure 5C:
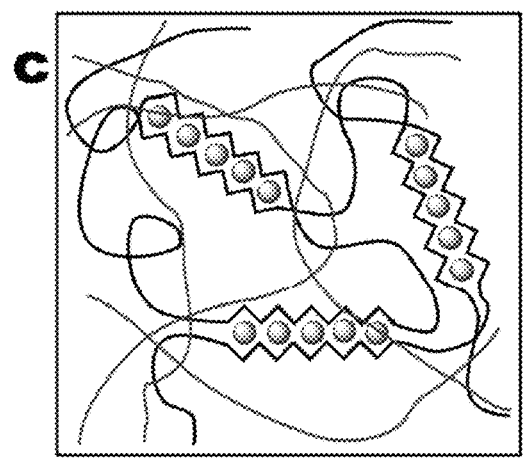
Figure 5D:
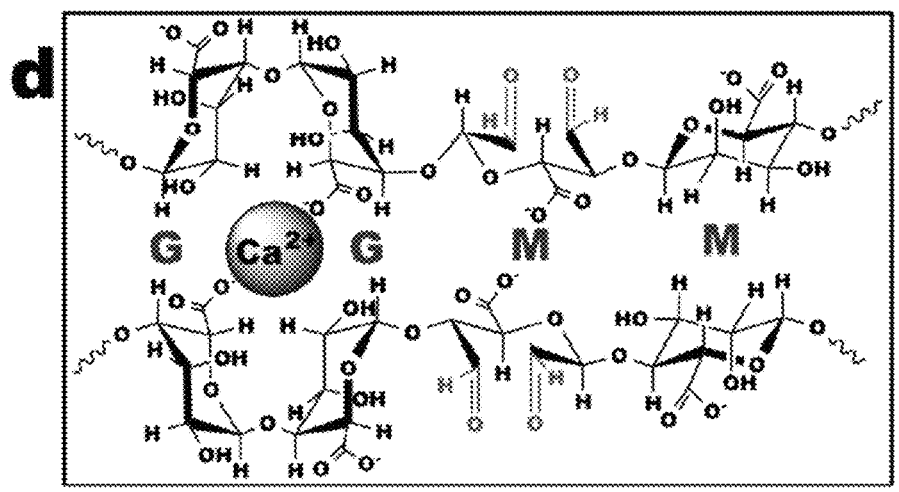
Figure 5E:
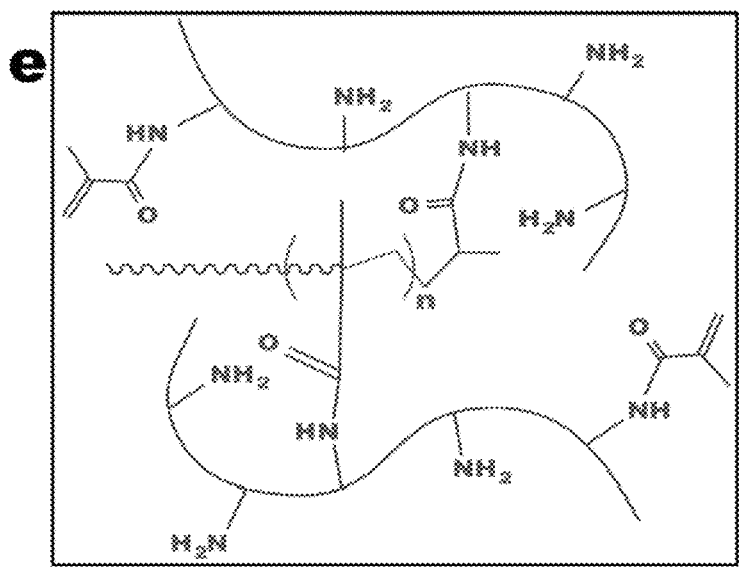
Figure 5F:
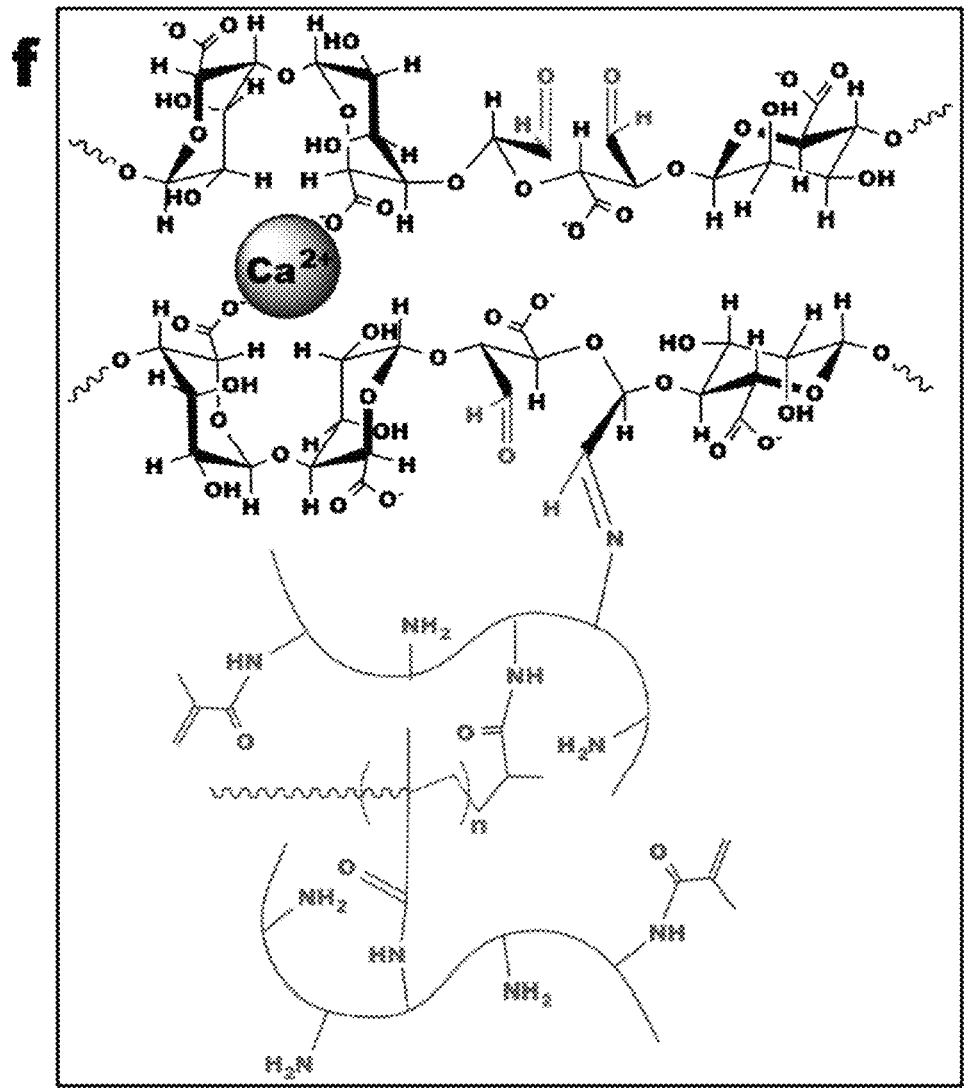

The overall strategy for the formation of the IPN-structured hydrogels is depicted in FIG. 1. Alginate contains repeating units of 1,4-linked β-d-mannuronic acid (M unit) and α-1-guluronic acid (G unit). The G units across different alginate macromers can form ionic crosslinks with divalent cations such as $Ca^{2+}$ in aqueous solution, resulting in a polymer network (FIG. 1 and FIGS. 5a and 5d). To generate a hydrogel with GelMA, which was chosen because of it high elasticity under deformation, crosslinked networks are formed by photocrosslinking of the methacrylate groups with low level UV light and a photoinitiator (FIG. 1 and FIGS. 5b and 5e). The completeness of GelMA photocrosslinking was verified with $^1$H-NMR. After photocrosslinking, the disappearance of the vinyl methylene peaks in $^1$H-NMR spectra (between 5.5 and 6 ppm) indicates the complete reaction of the methacrylated groups. Alginate can be oxidized (OA) to form aldehyde groups in its polymer backbone, which enhances the rate of hydrolytic degradation of resulting hydrogels. Mixing the two macromers together results in imine-bond formation via Schiff base reaction between the aldehyde groups of the OA and the amine groups of the GelMA (FIGS. 5c and 5f). 54.9% of OA-2 aldehydes and 29.4% of OA-5 aldehydes reacted with amine groups of GelMA to form imine bonds as determined by $^1$H-NMR. Homogeneity of the IPN-structured hybrid hydrogels at the microscale was confirmed with fluorescence microscopy.

Figure 2A:
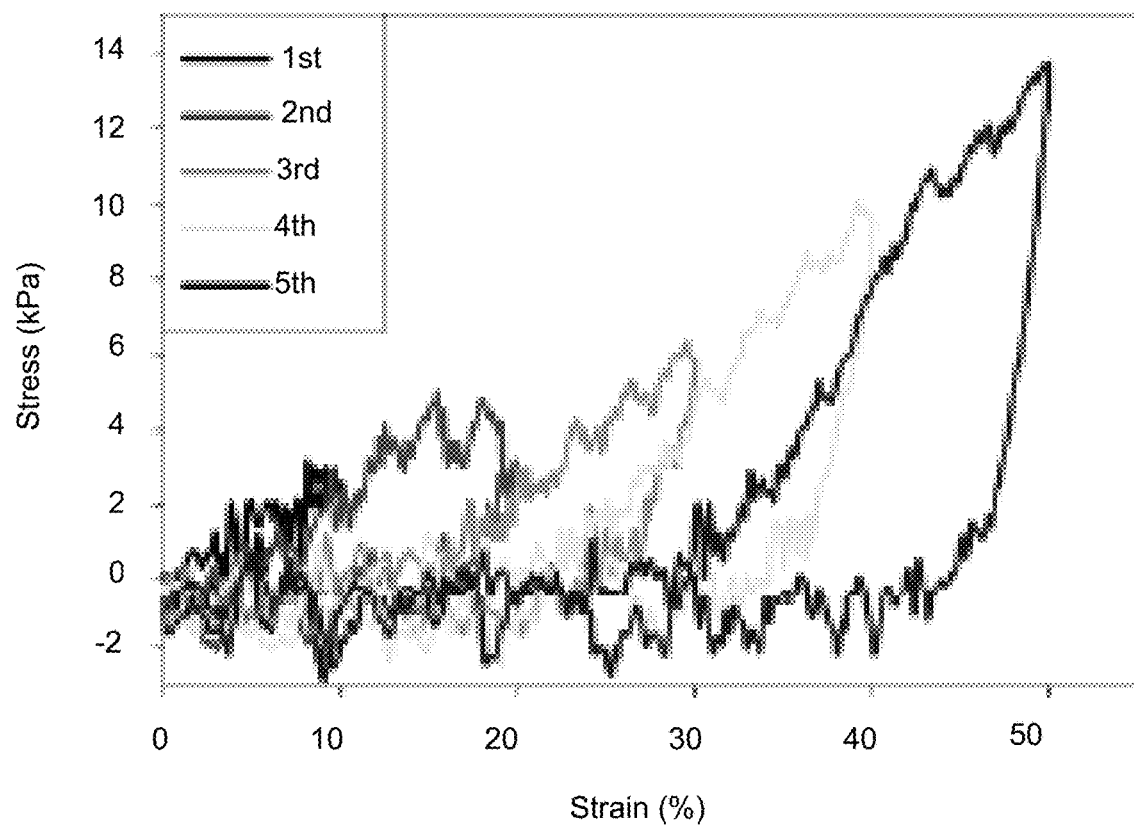
FIGS. 2(A-I) illustrate stress-strain hysteresis plots of A) Non-oxidized alginate (ALG, 1.25 w/v %), B) theoretically 2% oxidized alginate (OA-2, 1.25 w/v %), C) GelMA (10 w/v %), D) ALG (1.25 w/v %)/GelMA (10 w/v %), E) OA-2 (1.25 w/v %)/GelMA (10 w/v %), F) theoretically 5% oxidized alginate (OA-5, 1.25 w/v %)/GelMA (10 w/v %), and G) theoretically 10% oxidized alginate (OA-10, 1.25 w/v %)/GelMA (10 w/v %) hybrid hydrogels for five cycles of deformation. Strain increased by 10% increments with each successive cycle from 10% to 50%. Fatigue properties of IPN-structured hybrid hydrogels. Stress-strain hysteresis plots of H) ALG/GelMA and OA-5/GelMA hybrid hydrogels during the 1st and 1000th cycle of loading and unloading, and I) a OA-5/GelMA hybrid hydrogel during the 10000th and 20000th cycles to a strain magnitude of 10%.
Figure 2B:
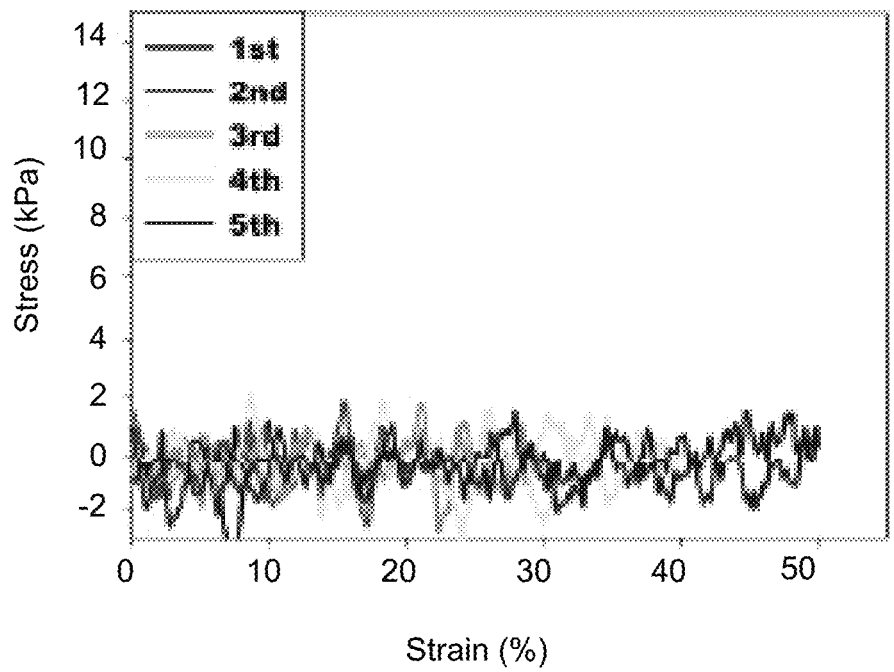
Figure 2C:
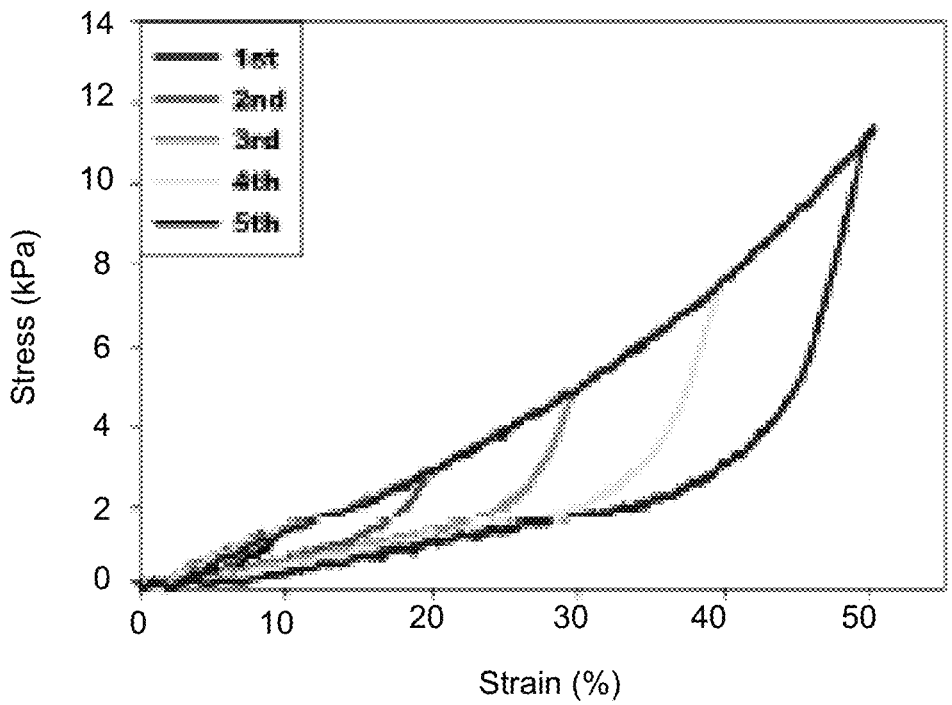
Figure 2D:
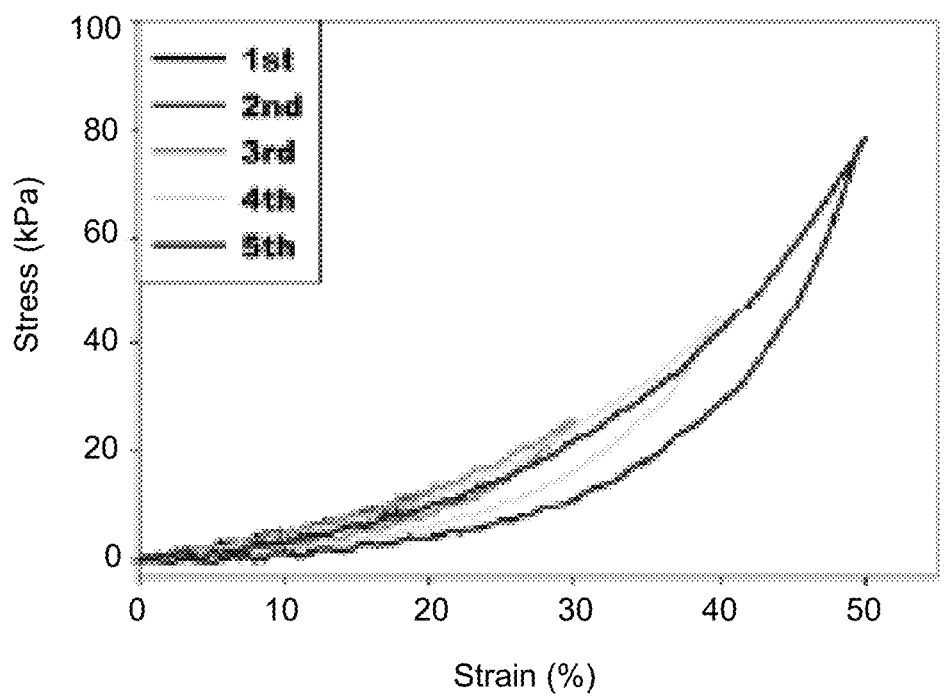
Figure 2E:
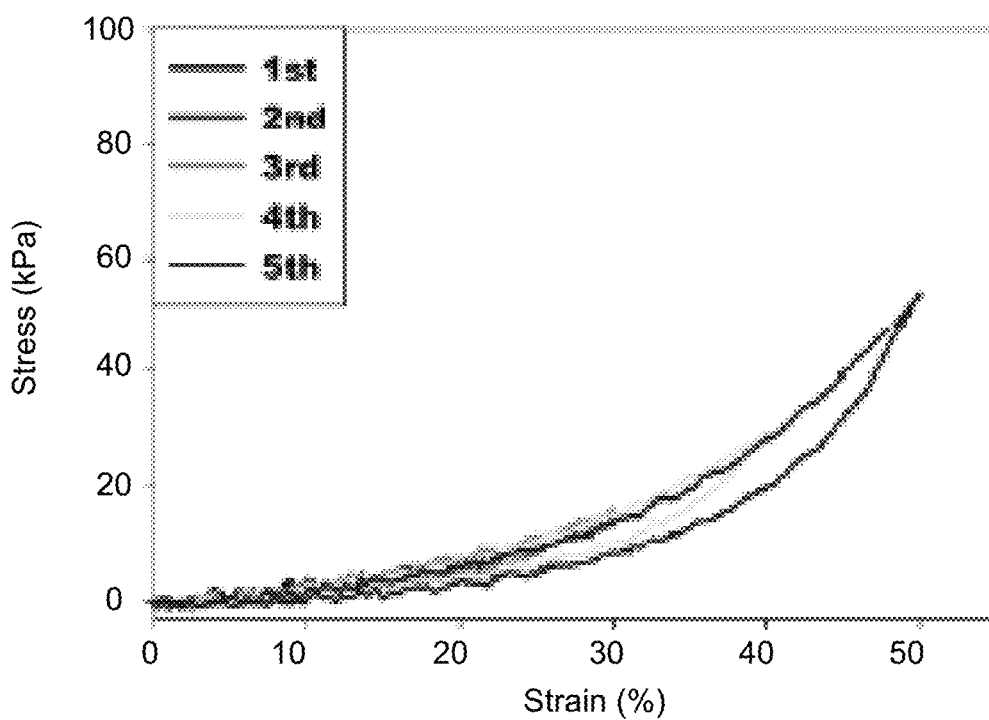
Figure 2F:
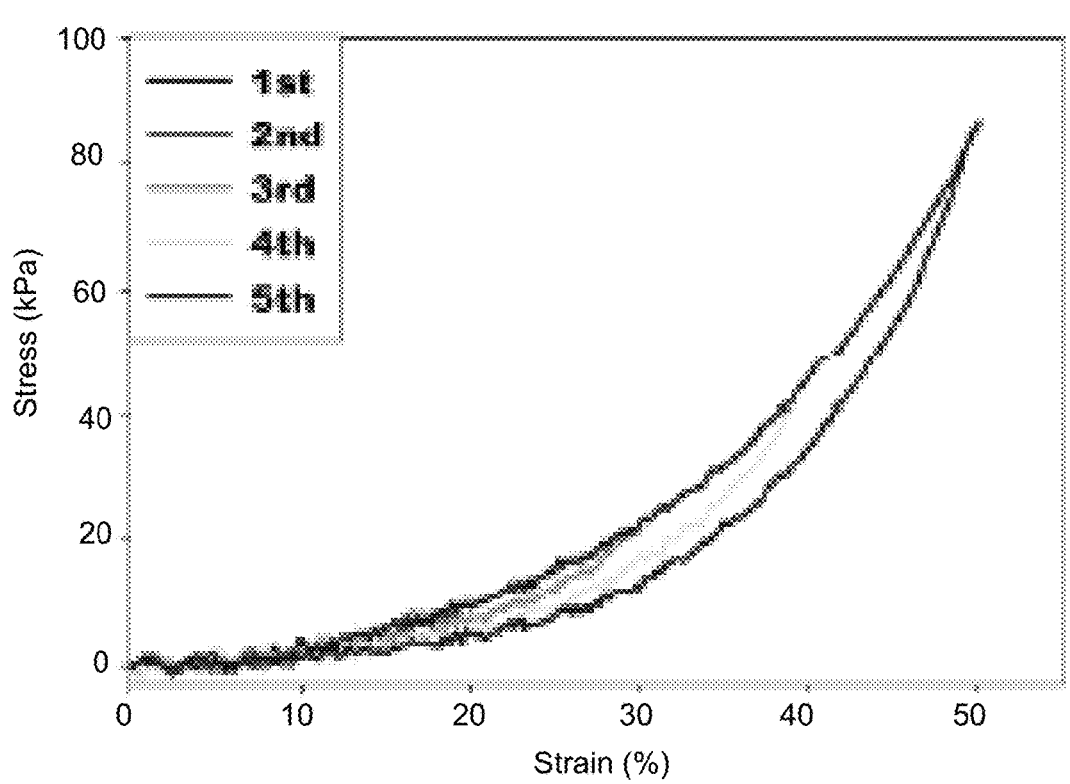
Figure 2G:
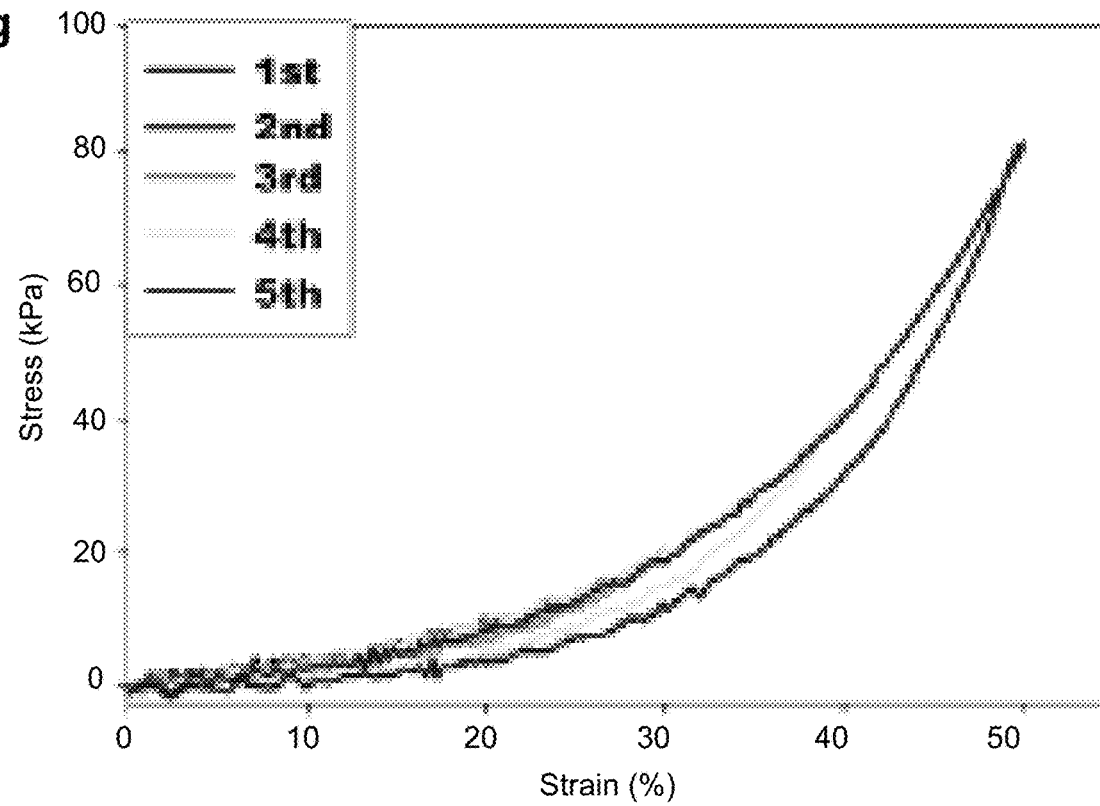
Figure 2H:
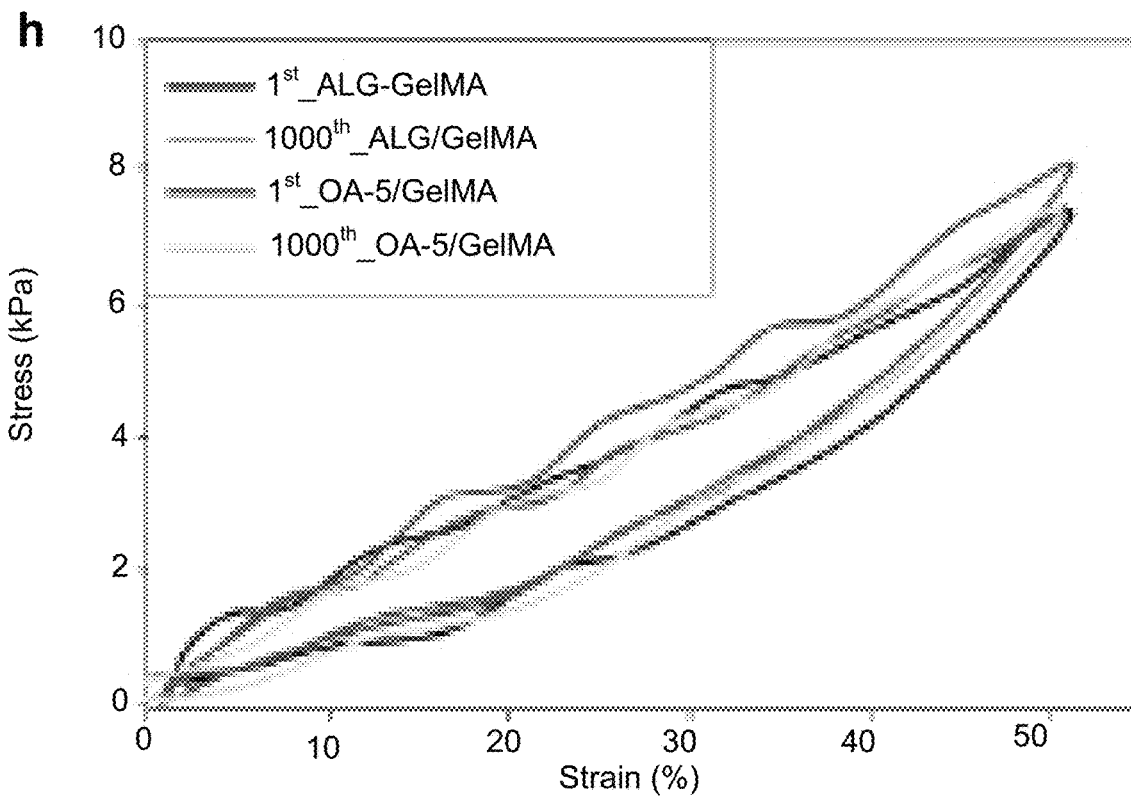
Figure 2I:
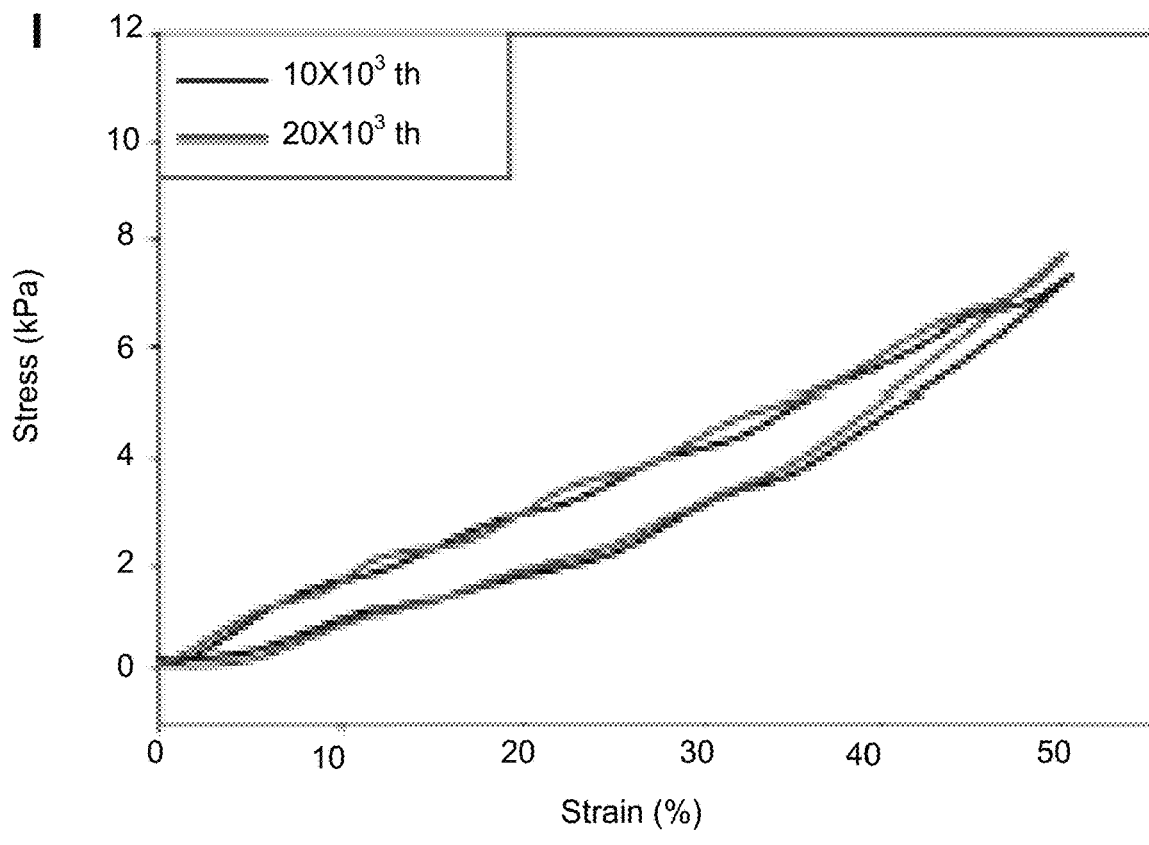
Figure 6A:
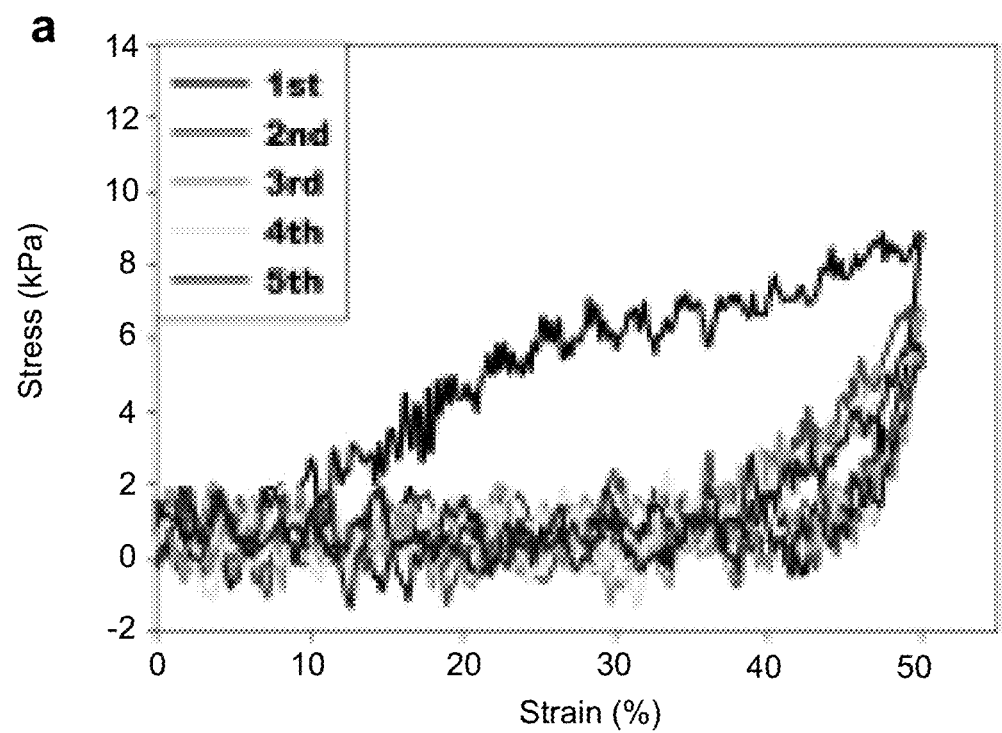
FIGS. 6(A-G) illustrate stress-strain hysteresis plots of A) ALG B) OA-2 C) GelMA D) ALG/GelMA E) OA-2/GelMA F) OA-5/GelMA G) OA-10/GelMA hybrid hydrogels under the five cycles of deformation at 50% strain.
Figure 6B:
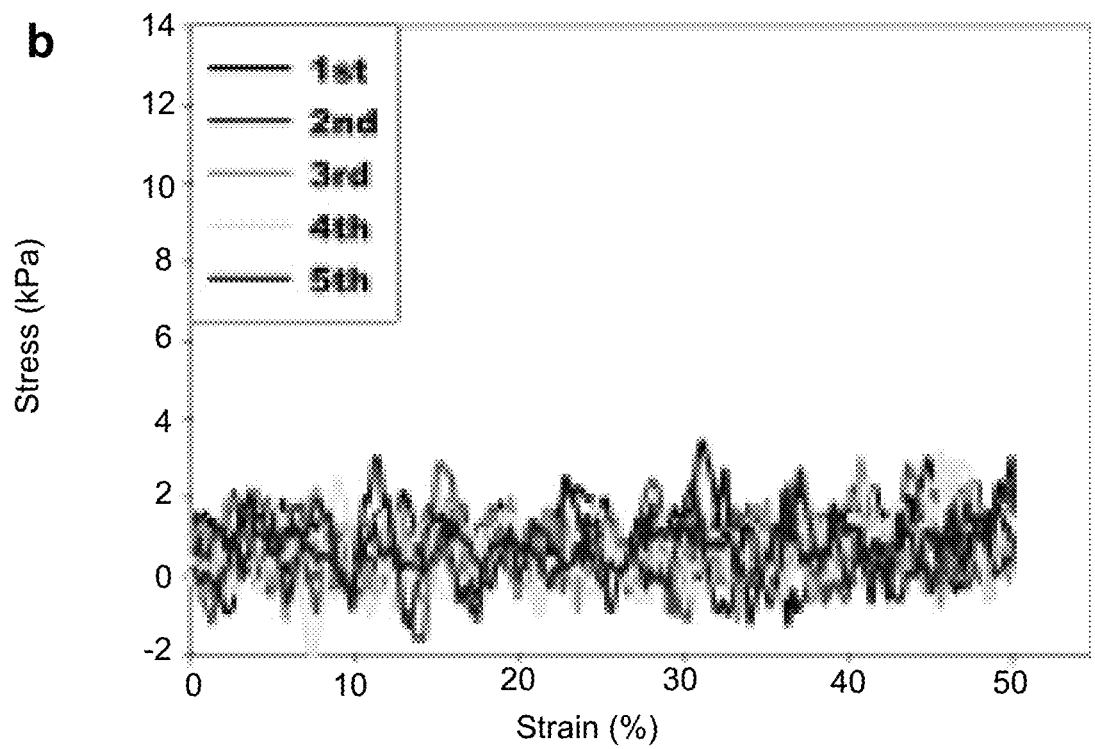
Figure 6C:
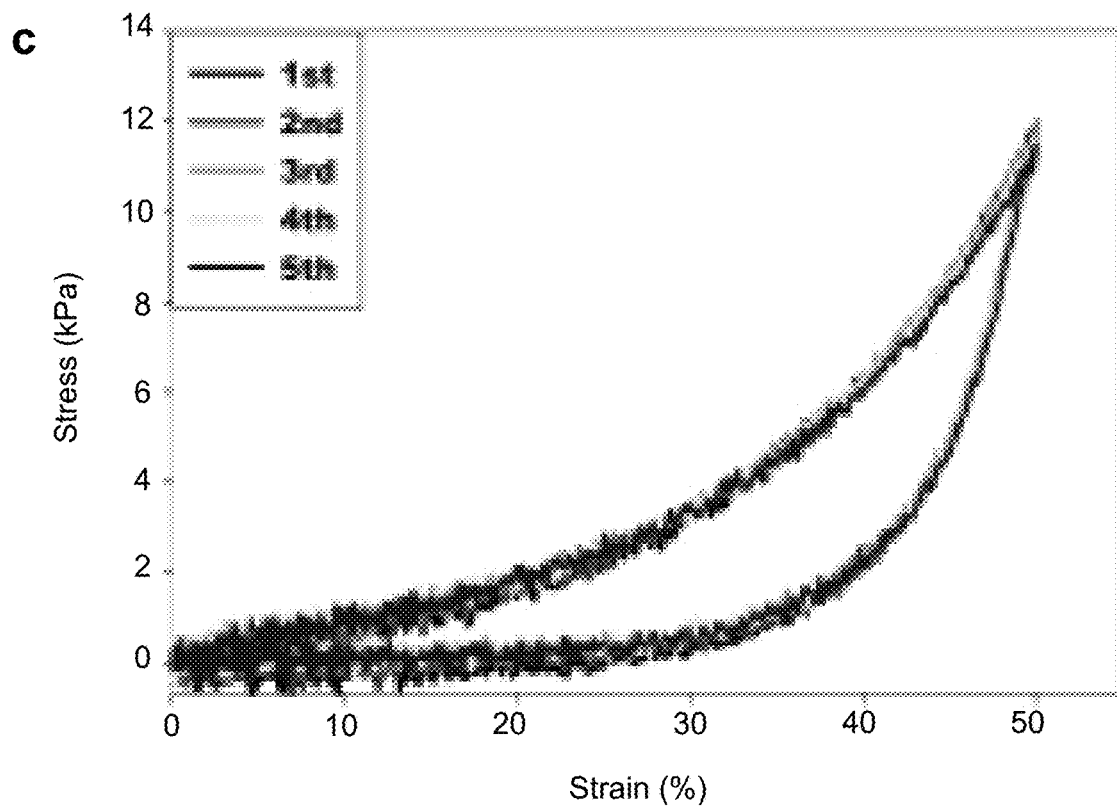
Figure 6D:
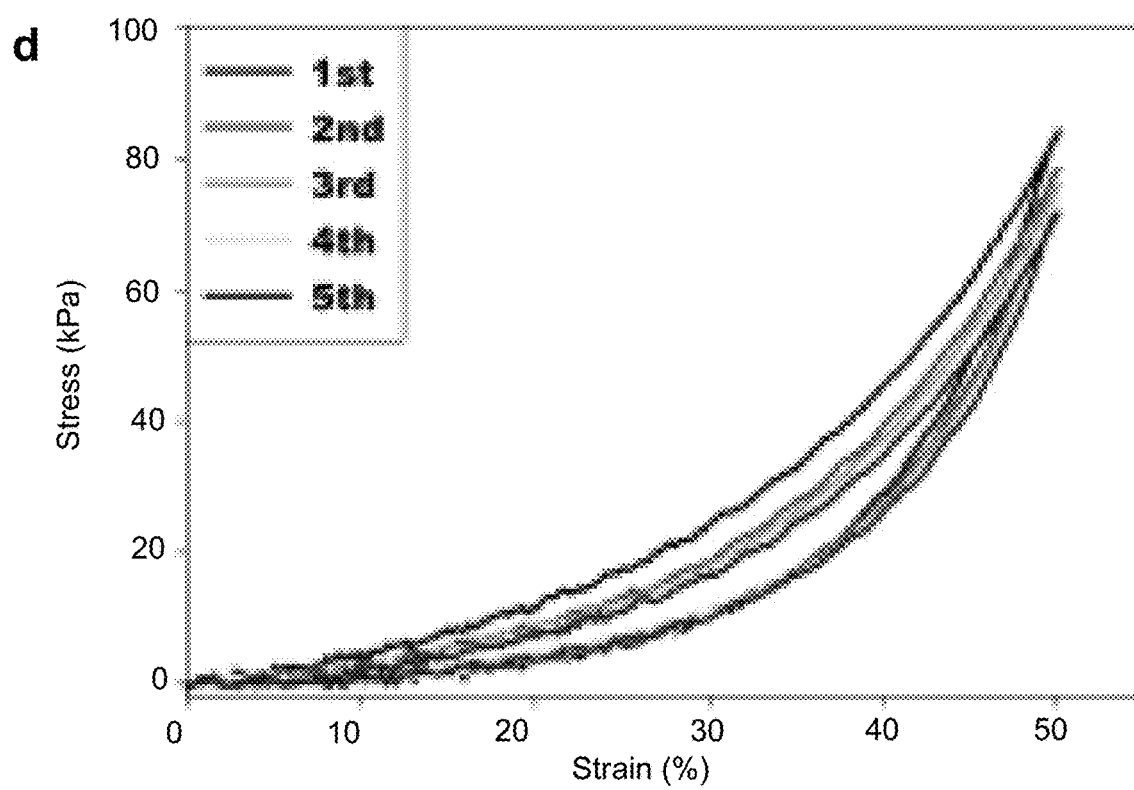
Figure 6E:
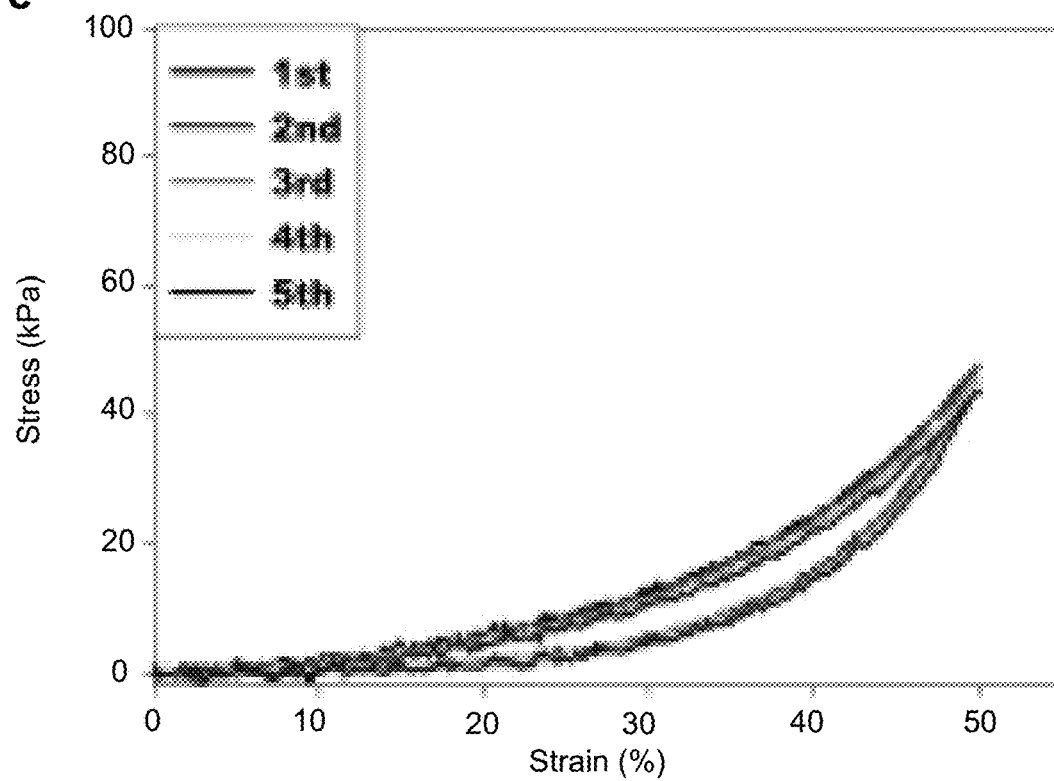
Figure 6F:
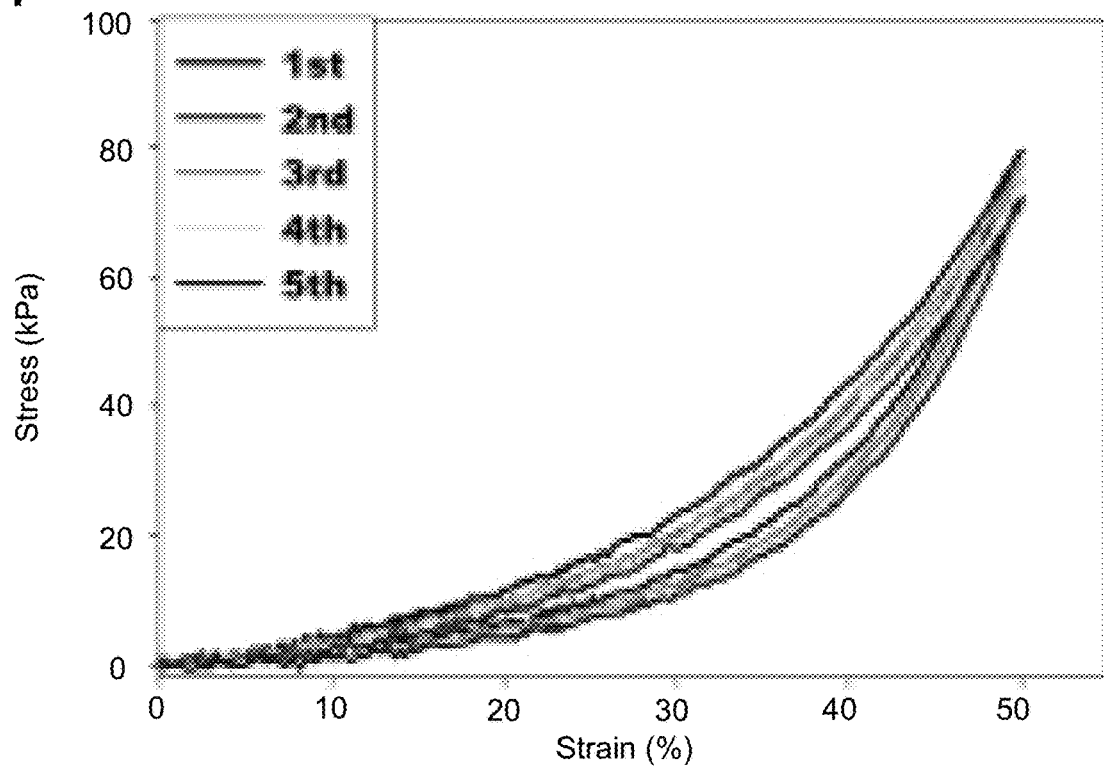
Figure 6G:
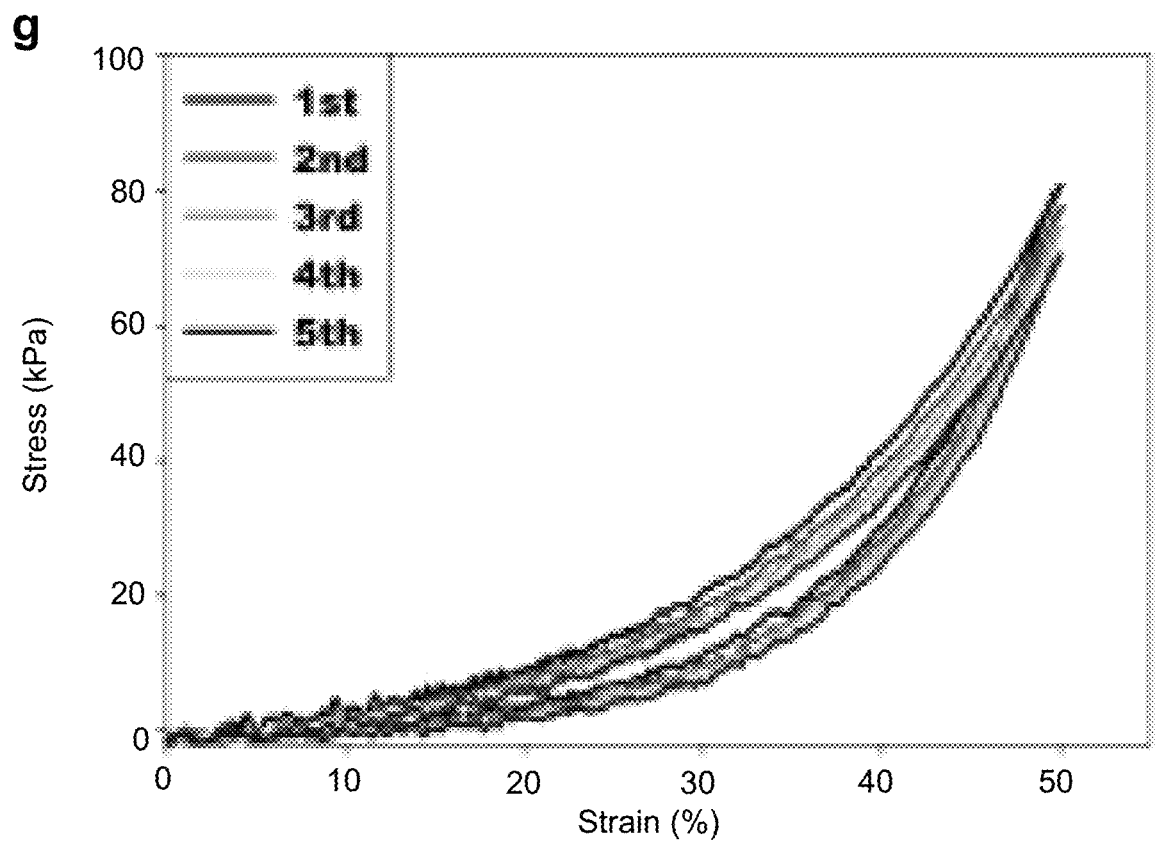
Figure 7A:
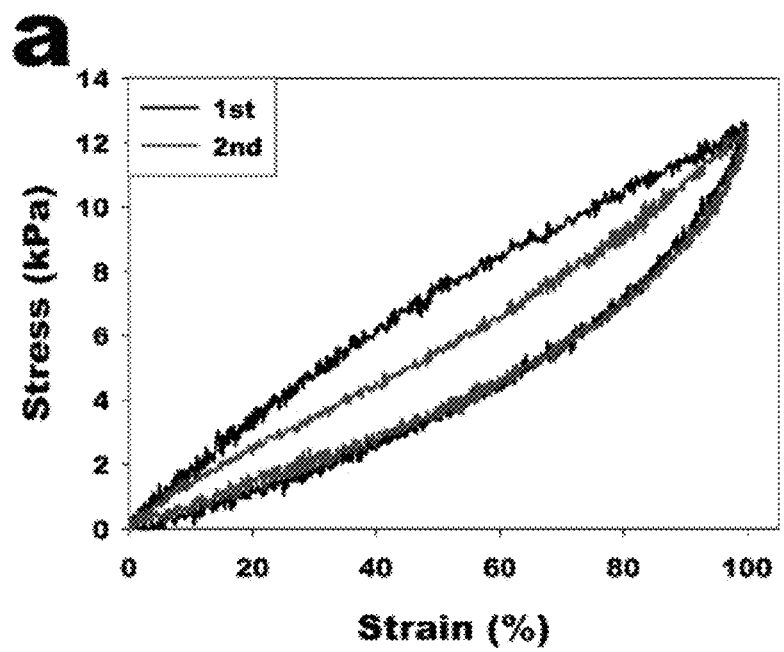
FIGS. 7(A-C) illustrate stress-strain hysteresis plots of the A) ALG/GelMA B) OA-2/GelMA and C) OA-5/GelMA IPN-structured hybrid hydrogels under the two cycles of tensile deformation (100% strain).
Figure 7B:
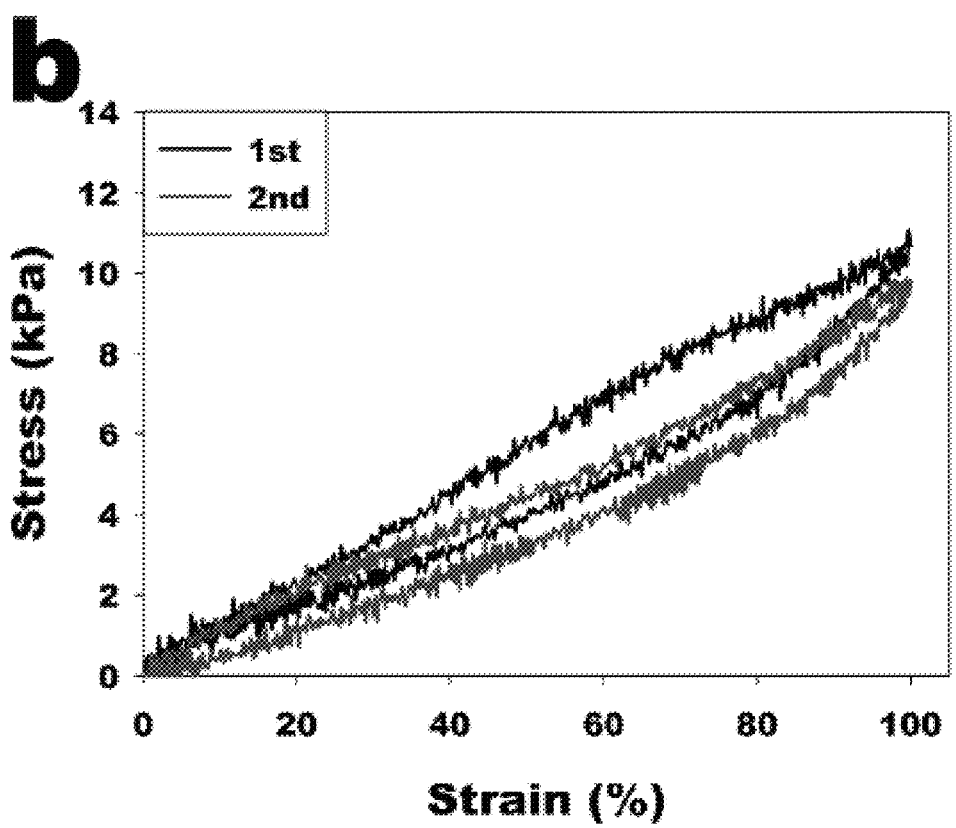
Figure 7C:
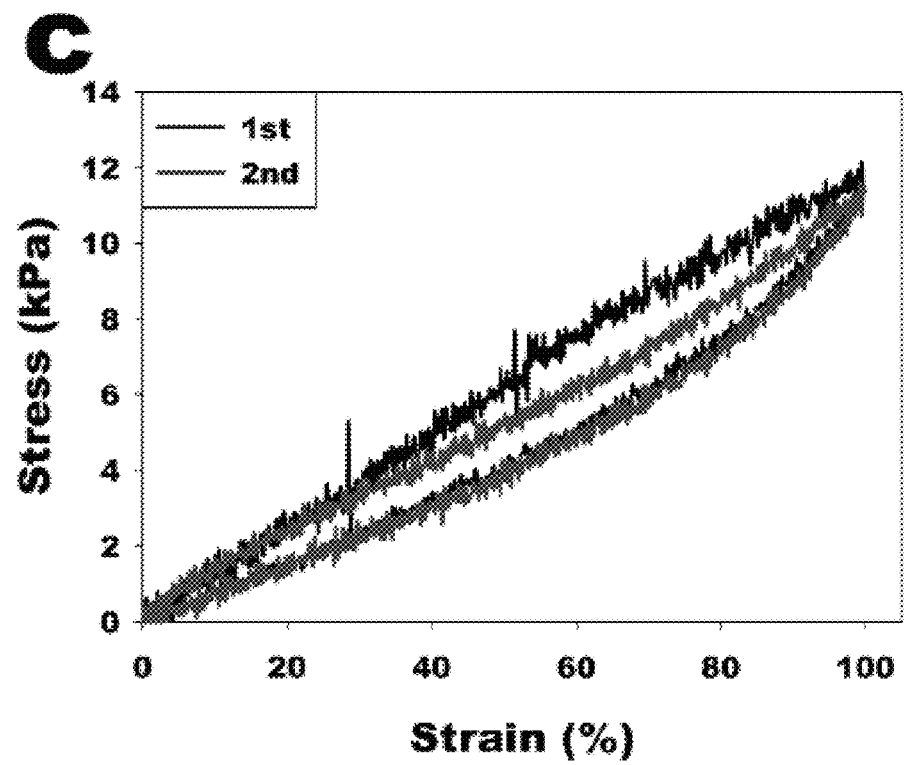

While ionically crosslinked alginate hydrogels were mechanically weak and had low elasticity, the IPN-structured hybrid hydrogels were tough, flexible and highly elastic. When the elastic properties of hydrogels were evaluated by unconfined cyclic compression testing up to 50% strain, the non-oxidized alginate hydrogels (ALG) exhibited pronounced hysteresis and significant permanent deformation after each loading and unloading cycle (FIG. 6a). The OA hydrogels were too weak to examine their elastic behavior (FIG. 2b and FIG. 6b). The GelMA hydrogels also showed pronounced hysteresis, but fully recovered their original thickness after unloading (FIG. 2c). Despite the high elasticity of GelMA hydrogels, their poor ability to withstand loads limits their use in applications that required mechanical strength. Although the IPN-structured hybrid hydrogels showed pronounced hysteresis as well, unlike the alginate hydrogels, they all fully recovered their original thickness immediately after each unloading. Additionally, mechanical properties of the IPN-structured hybrid hydrogels were greatly enhanced compared to hydrogels comprised only of a single biopolymer, alginate or GelMA hydrogels (FIGS. 2(a-g) and FIGS. 6(a-g)). The highly elastic nature of the IPN-structured hybrid hydrogels was further confirmed by cyclic tensile testing (FIG. 7). While the IPN-structured elastomeric hybrid hydrogels responded with excellent shape recovery to physiologically extreme strain levels, fatigue resistance of the hydrogels to a high number of moderate strain cycles may be more relevant to their use in tissue engineering strategies. To further investigate the long-term resilience and fatigue properties of the IPN-structured elastomeric hybrid hydrogels, unconfined cyclic compression tests at 10% strain for up to 20000 cycles were performed. The IPN-structured elastomeric hybrid hydrogels exhibited extraordinarily high resistance to fatigue (FIGS. 2(h, i)). ALG/GelMA and OA-5/GelMA hybrid hydrogels exhibited negligible hysteresis and fully recovered immediately after 1000 cycles of loading and unloading. In addition, OA-5/GelMA fully recovered its original thickness even after 10000 and 20000 cycles of loading and unloading (FIG. 2i). These results indicate that these IPN-structured hybrid hydrogels have great potential as biomaterials for biomedical applications that require full recovery from large strains and/or long term cyclic compression.

Figure 3A:
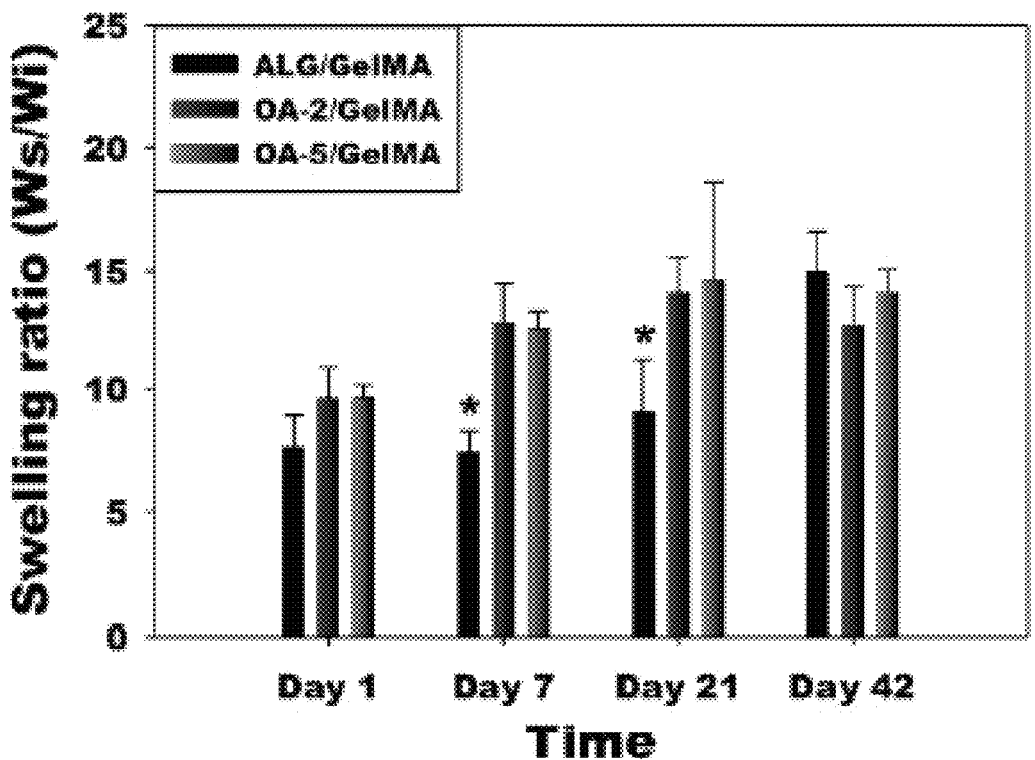
FIGS. 3(A-F) illustrate graphs and plots showing hydrogel physical property changes over time. A) Swelling (N=3), B) degradation (N=3), and C) modulus (N=3) of IPN-structured elastomeric hybrid hydrogels. Stress-strain curves of D) ALG/GelMA E) OA-2/GelMA and F) OA-5/GelMA hybrid hydrogels over time. *p<0.05 compared with the other groups at a specific time point. **p<0.05 compared with the other time points within a specific group.
Figure 3B:
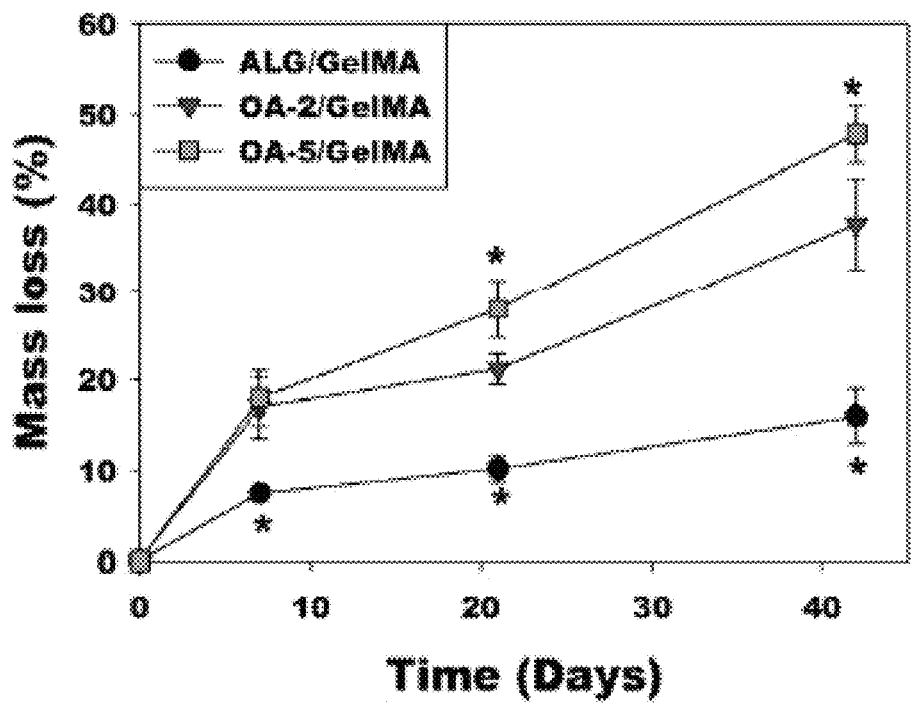
Figure 3C:
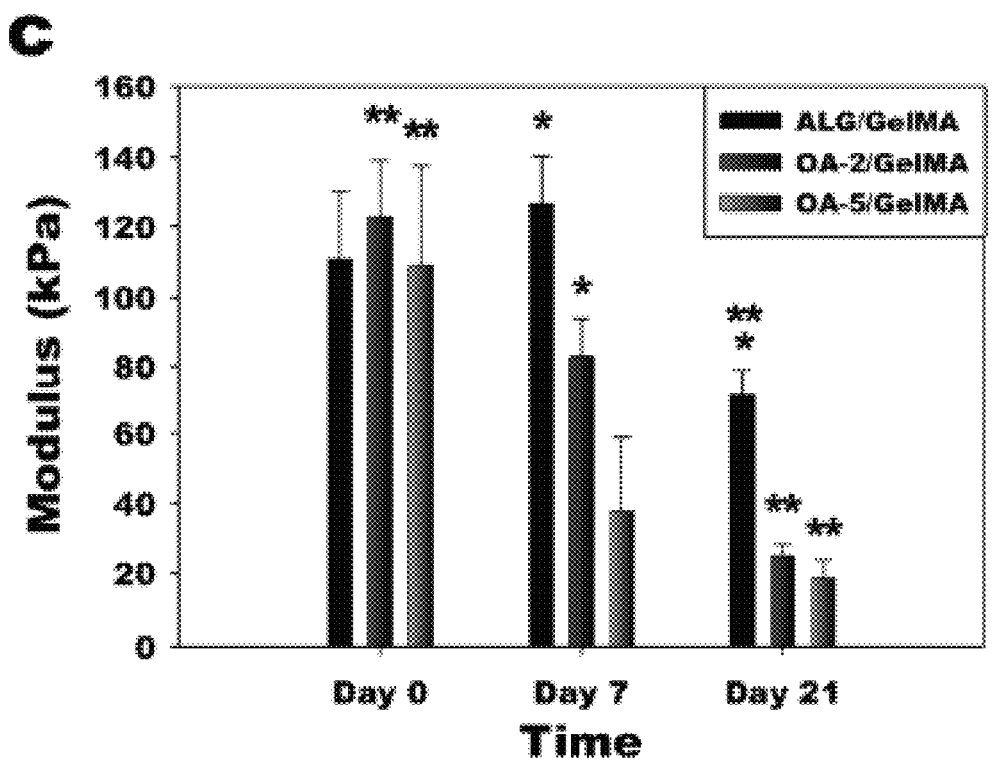
Figure 3D:
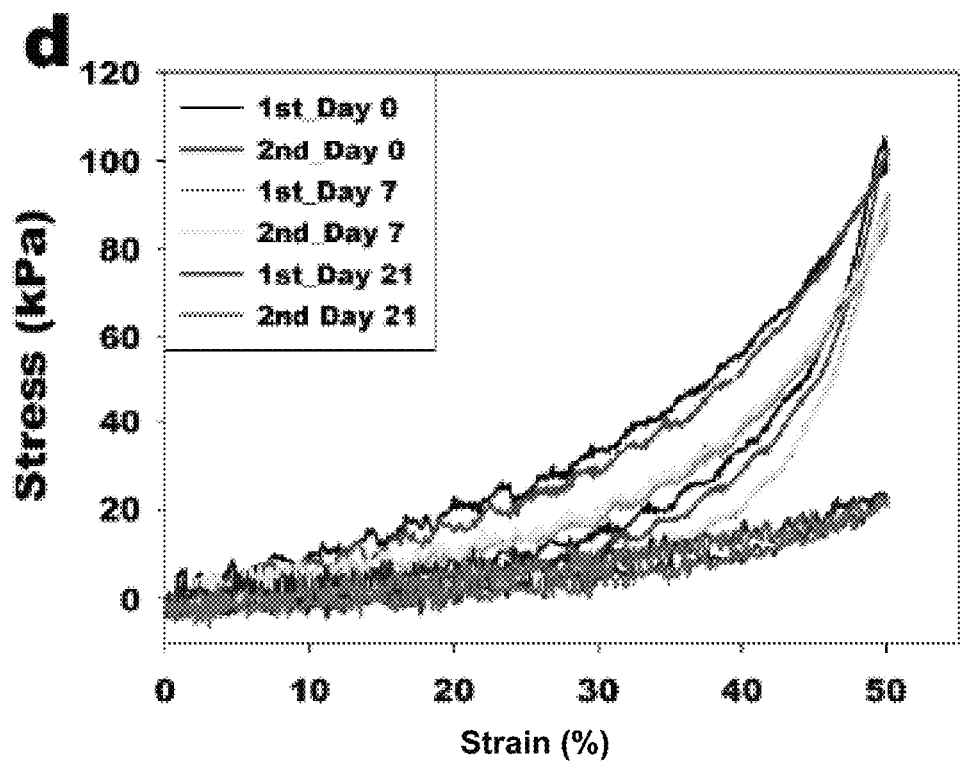
Figure 3E:
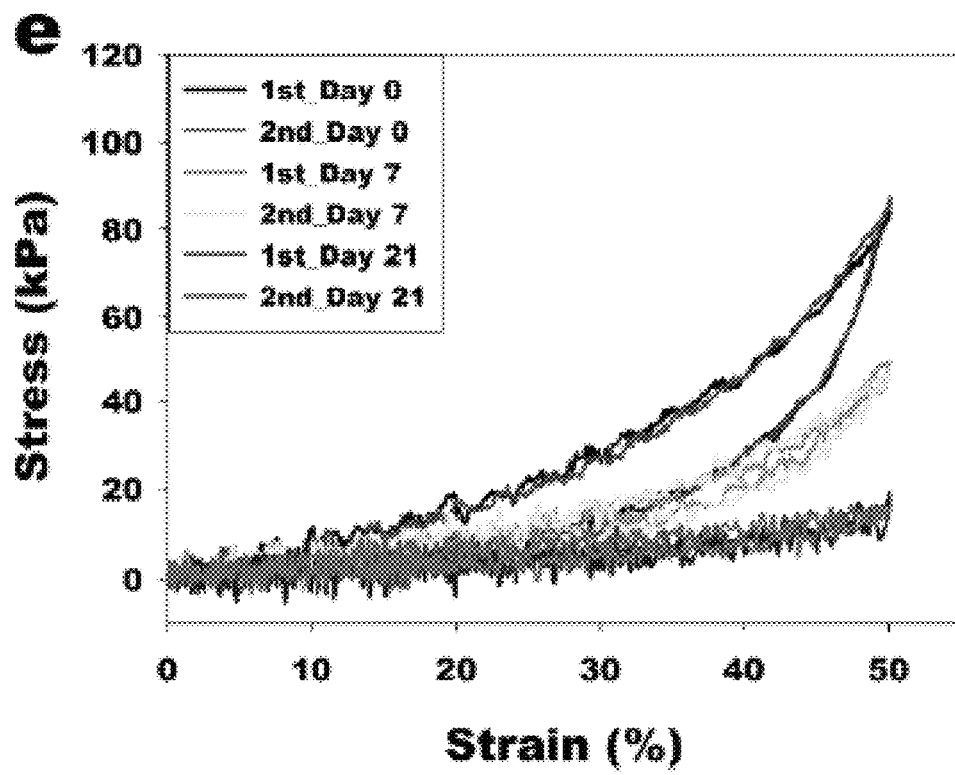
Figure 3F:
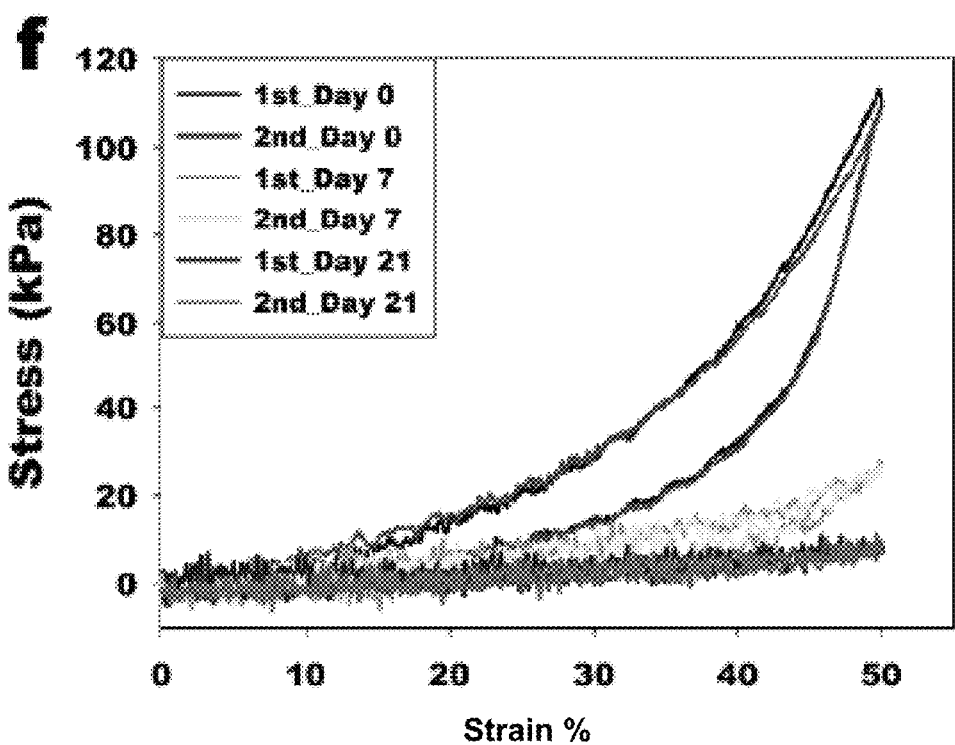

Since hydrogel degradation can affect the mechanical properties of materials, unconfined cyclic compression tests (2 cycles) were performed over time to evaluate potential changes in the elasticity of the IPN-structured hybrid hydrogels. The elastic modulus of IPN-structured hybrid hydrogels decreased during the course of degradation (FIG. 3c). As the oxidation level of alginate increased, the modulus decreased at day 7. After 21 days, the moduli of OA/GelMA hybrid hydrogels were significantly lower than that of ALG/GelMA hybrid hydrogels. Although the stiffness of OA/GelMA IPN-structured hybrid hydrogels rapidly changed during degradation, they exhibited excellent resilience (FIG. 3(e-f)). ALG/GelMA IPN-structured hybrid hydrogels also maintained their high elasticity even after 3 weeks of degradation (FIG. 3d). All IPN-structured hybrid hydrogels recovered from applied compressive strain (50%) to their original thickness as evidenced by representative cyclic loading/relaxation curves taken over the course of 21 days. This result indicates that the all IPN-structured elastomeric alginates/GelMA hybrid hydrogels are biomaterials that retain their high elasticity in response to large strains during degradation for at least 21 days.

Figure 4A:
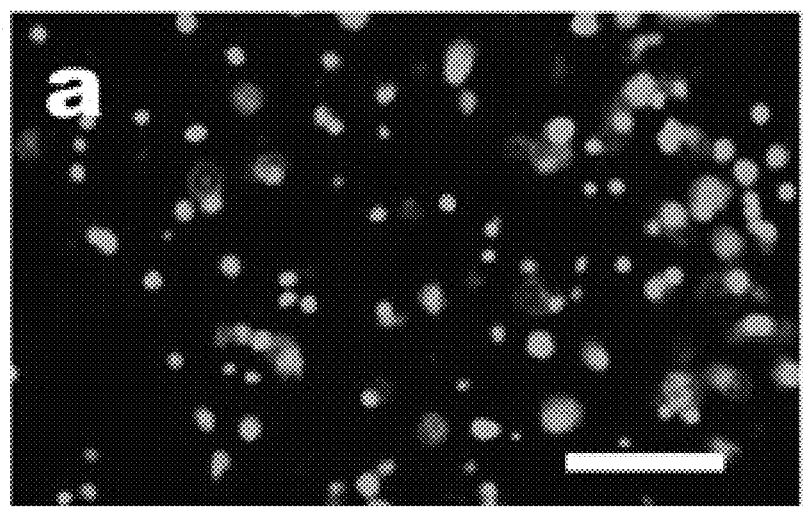
FIGS. 4(A-M) illustrate images and graphs showing IPN-structured elastomeric hydrogels are cytocompatible, and mechanical stimulation on hMSC encapsulated IPN-structured elastomeric hybrid hydrogels enhances hMSC osteogenesis. Live/Dead staining of encapsulated hMSCs in IPN-structured elastomeric hybrid ALG/GelMA (A and C), OA-2/GelMA (B and E), and OA-5/GelMA (C and F) hydrogels at day 0 (A, B and C) and day 14 (D, E, and F). The scale bars indicate 100 µm. G) Quantification of DNA content of IPN-structured elastomeric hybrid ALG/GelMA, OA-2/GelMA and OA-5/GelMA hydrogel/hMSC constructs over time (N=3). *p<0.05 compared with the other groups at a specific time point. Quantification of H) DNA and I) ALP/DNA (N=4) in hMSCs encapsulated within hydrogels after 28 days culture in osteogenic differentiation media. *p<0.05 compared with Stimulation group at a specific time point. p>0.05 and *p>0.05 compared with Day 7 and Day 28, respectively, within a specific group, otherwise p<0.05. Mineralization of cell-hydrogel constructs analyzed by Alizarin red staining of J) bulk (upper disks: Stimulation group and lower disks: No Stimulation group; The scale bar indicates 10 mm.) and sectioned K) Stimulation and L) No Stimulation constructs (The scale bars indicate 200 µm), and M) quantification of calcium content (N=4) in the constructs. *p<0.05 compared with Stimulation group at a specific time point. **p>0.05 compared with Day 7 within a specific group, otherwise p<0.05.
Figure 4B:
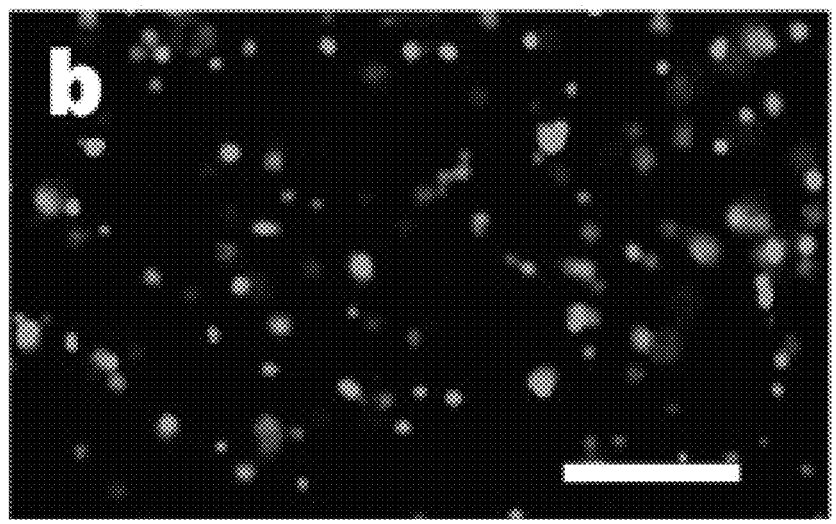
Figure 4C:
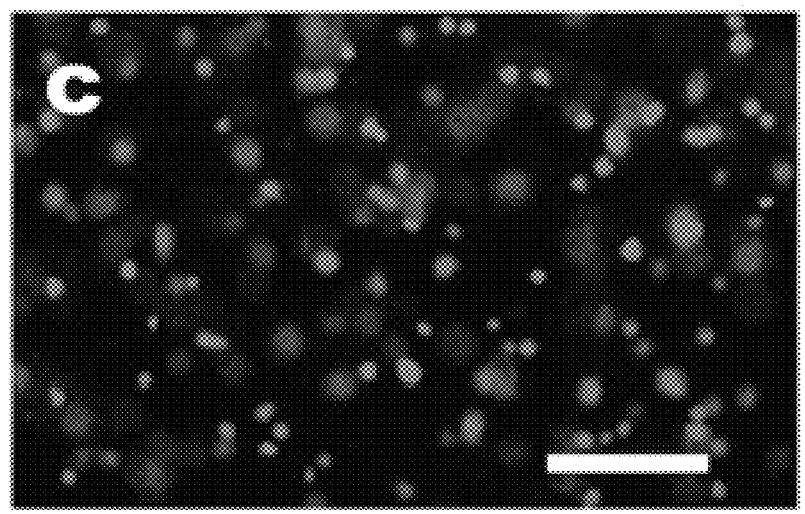
Figure 4D:
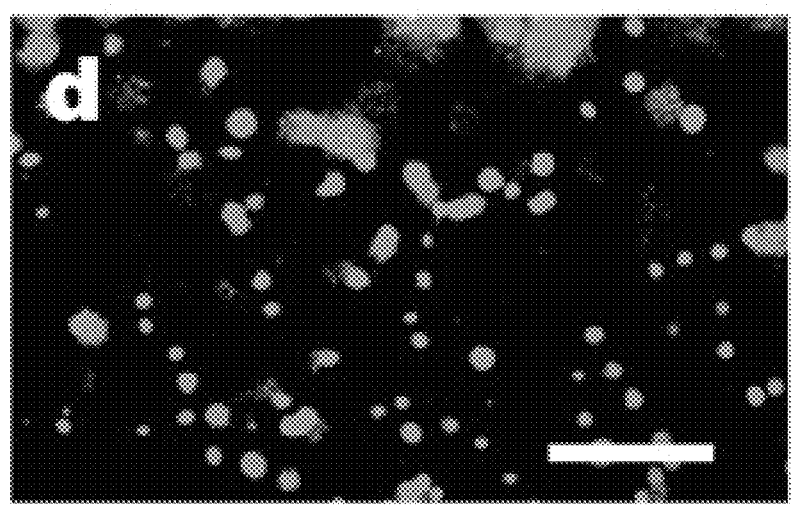
Figure 4E:
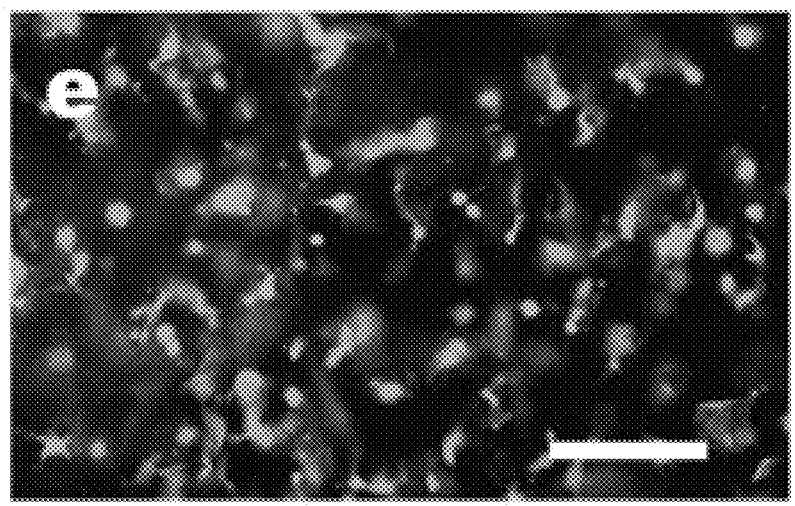
Figure 4F:
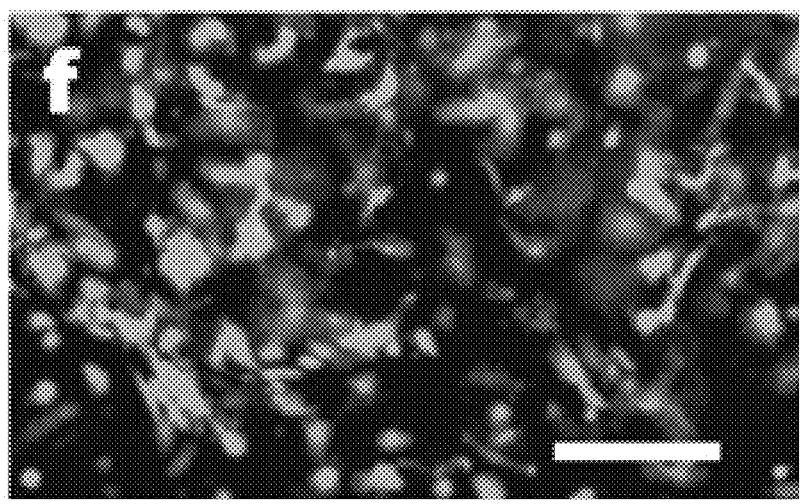
Figure 4G:
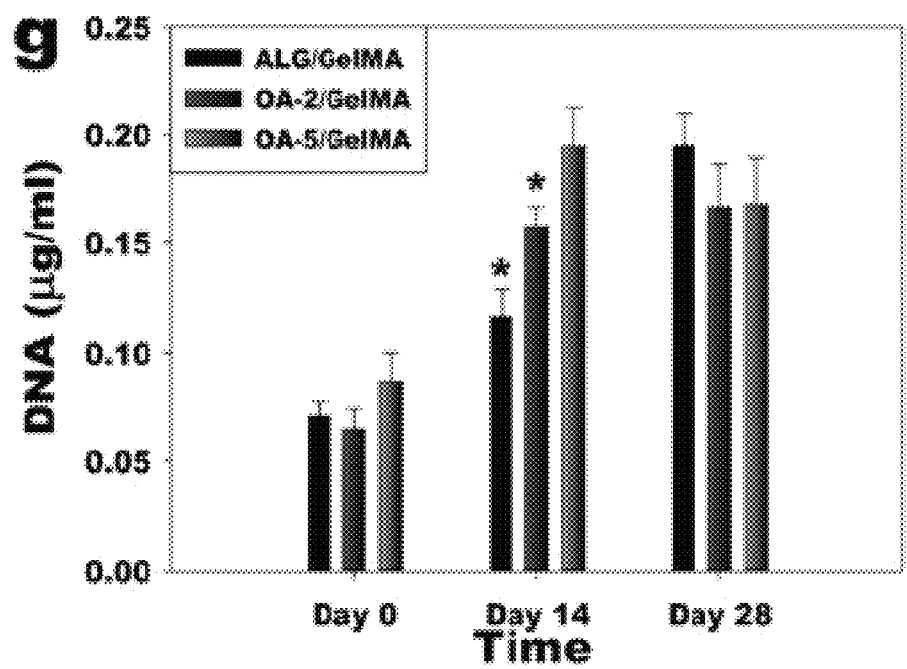

Several elastomeric alginate hydrogels based on IPN-structure have been developed. While these hydrogels exhibited high elasticity in response to both applied tension and compression, none of them possessed good cytocompatibility or permitted long-term survival of cells encapsulated within them. To verify that the IPN-structured elastomeric alginate/GelMA hydrogels were cytocompatible and could be used as 3D matrices for long-term culture of viable encapsulated cells, human bone marrow-derived mesenchymal stem cells (hMSCs) were encapsulated within them and cultured in serum containing media. High hMSC viability was observed throughout all groups for 14 days (FIGS. 4(a-f)), indicating that the mixing and photocrosslinking process, the macromers, the IPN-structured elastomeric hydrogels themselves and their degradation products are non-toxic to the cells. Quantifying DNA content of the cell-laden IPN-structured elastomeric hybrid hydrogels demonstrated that cells proliferated within the gels, reaching a more than 2-fold increase of over day 0 values after 14 and 28 days for the OA/GelMA and ALG/GelMA conditions, respectively (FIG. 4g). The hMSCs encapsulated in the OA/GelMA hydrogels exhibited a significantly faster growth rate with greater cell spreading up to 14 days (FIGS. 4e, f and g). A potential explanation may be that the greater swelling and faster degradation of IPN-structured OA/GelMA elastomeric hybrid hydrogels (FIGS. 2a and b) provided more space and weaker network formation, permitting increased cell spreading, migration and proliferation. Additionally, these physical changes may allow for improved transport of oxygen and nutrients, which are essential for cell survival and proliferation. This finding also corroborates other reports where increasing the biodegradation rate of hydrogels enhanced the proliferation of encapsulated cells.

Figure 4H:
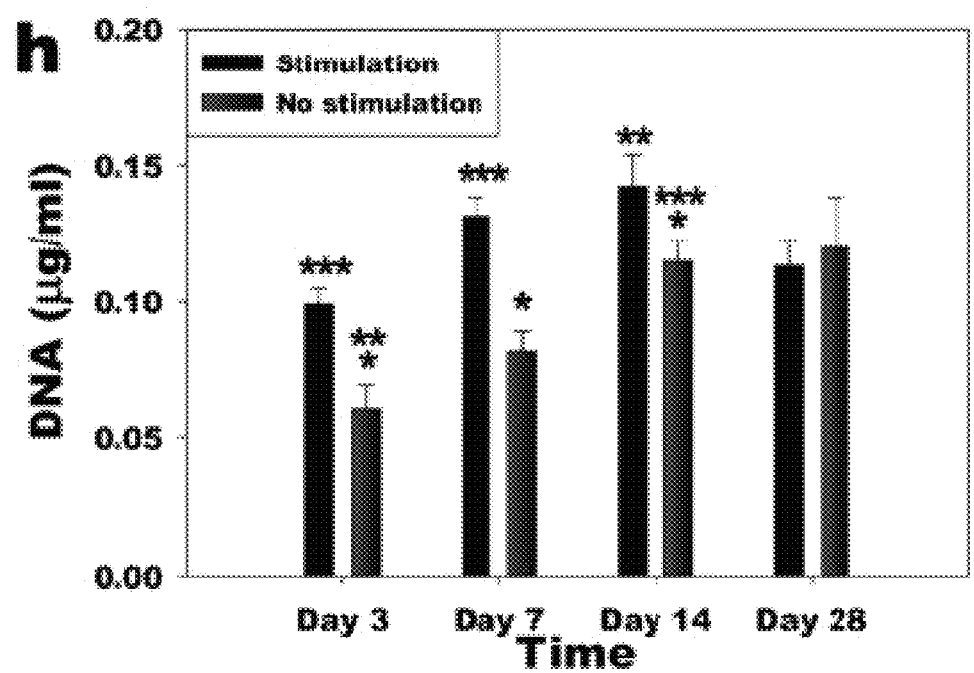
Figure 4I:
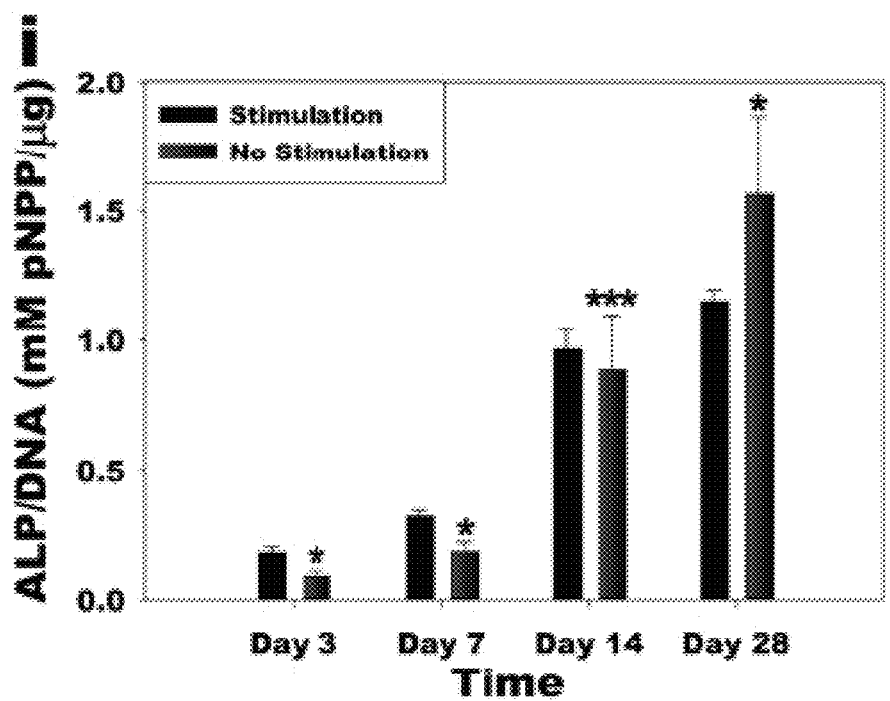
Figure 4J:
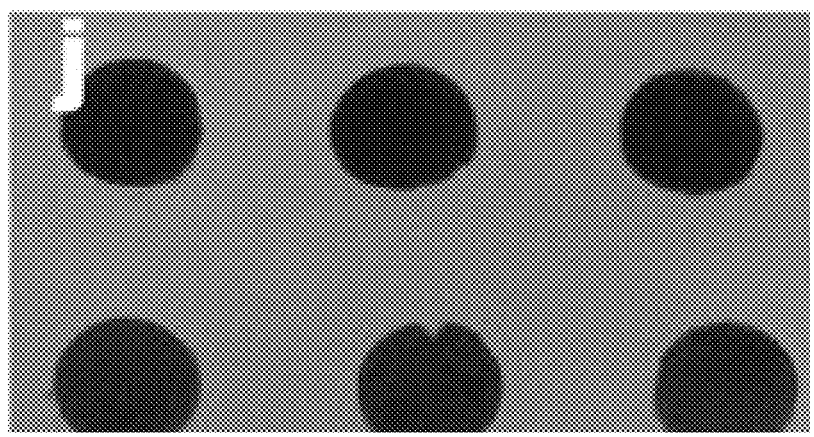
Figure 4K:
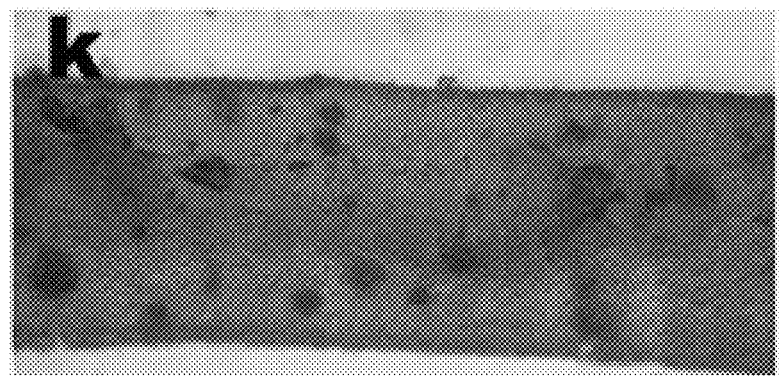
Figure 4I:
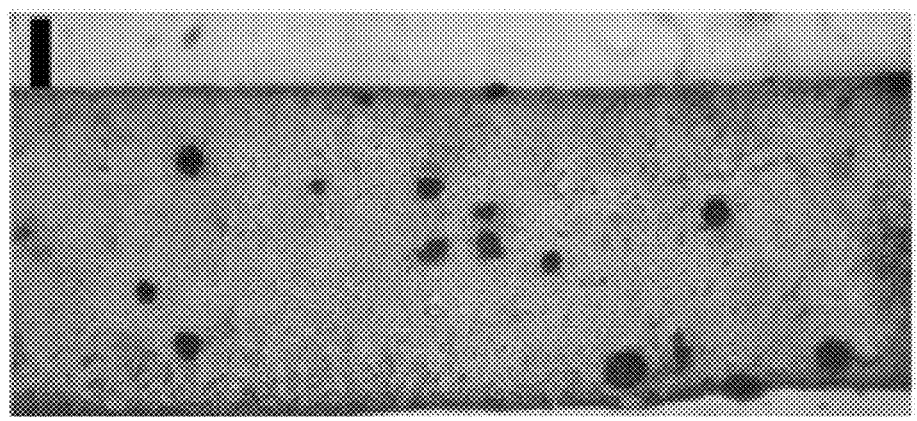
Figure 4M:
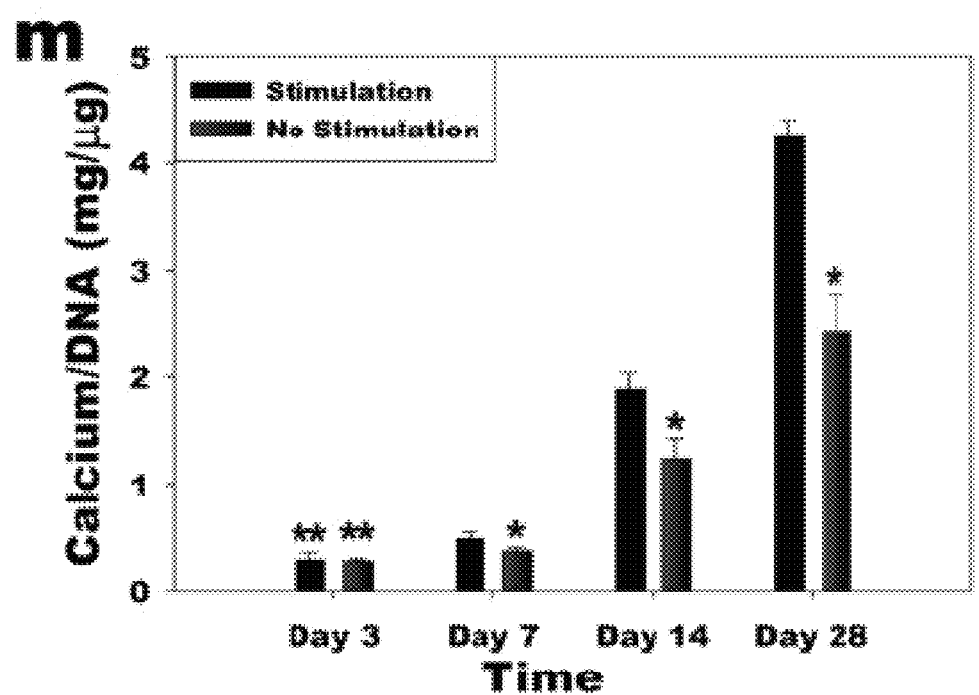

Cells are subjected to a variety of physical stresses in vivo, and these mechanical stimuli play a key role in controlling cell behaviors. Therefore, mechanical stimulation of cells in biomaterials is an area of increasing interest for tissue engineering and regenerative medicine applications. When mechanical stress is applied to hydrogels, this stress is transmitted to encapsulated cells and transduced into biochemical signals that can alter cell gene expression and function. Dynamic cyclic compression, for example, has been demonstrated to induce osteogenic differentiation of hMSCs within hydrogels and modulate bone-specific extracellular matrix synthesis, resulting in improved mechanical properties of engineered bone. Due to the non-elastomeric nature of most cytocompatible hydrogels, they may not be able to completely recover from deformation and effectively transmit the defined mechanical stimulation to encapsulated cells. Since elastomeric materials have the potential to efficiently transmit mechanical stimulation to cells, hMSCs were encapsulated in IPN-structured elastomeric alginate/GelMA hybrid hydrogels. These hydrogel constructs were cultured in osteogenic differentiation media under dynamic cyclic compression to investigate the effect of mechanical stimulation on the osteogenic differentiation of stem cells in this system. The number of encapsulated hMSCs significantly increased over 14 days as a result of mechanical stimulation of the IPN-structured elastomeric hybrid hydrogels compared to the No stimulation group as measured by DNA content (FIG. 4h). Cyclic compression may enhance the supply of nutrients and oxygen to the encapsulated hMSCs by perfusing media resulting in the increased cell proliferation. hMSC/hydrogel constructs were then evaluated for hMSC osteogenic differentiation by measuring alkaline phosphatase (ALP) activity, an early osteogenic differentiation marker. Compared to the No stimulation group, the ALP activity of encapsulated hMSCs in the Stimulation group was significantly higher at early time points (day 3 and 7), however, there was no significant difference between groups at day 14 (FIG. 4i). It is possible that ALP activity peeked in the Stimulation group between 14 and 28 days, as this osteogenic differentiation marker was higher in the No Stimulation group at the latter time point. Since mineralization of tissue engineered bone constructs is the definitive marker of stem cell osteogenic differentiation, calcium deposition in the hMSC/hydrogel constructs was visualized by Alizarin red S staining and quantified. Compared to the No Stimulation group, more intense Alizarin red staining was observed in the Stimulation group at day 28 (FIG. 4j-l). Calcium deposition increased over time in both groups and was significantly higher at days 7, 14 and 28 in the Stimulation group compared to the No Stimulation group (FIG. 4m), confirming the day 28 Alizarin red S staining results. These findings demonstrate that mechanical stimulation of the IPN-structured elastomeric hybrid hydrogels enhances osteogenic differentiation of encapsulated stem cells and resulted in bone-like mineralization of the extracellular environment.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, I claim:

1. A composition comprising:
a triple-network hydrogel having three types of crosslinking networks that includes crosslinked first natural polymer macromers with a first elasticity and a homogenously distributed interpenetrating network of crosslinked second natural polymer macromers having a second elasticity higher than the first elasticity, the triple-network hydrogel being cytocompatible, and, upon degradation, produce substantially non-toxic products,
wherein the first polymer macromers are oxidized alginates and the second polymer macromers are acrylated and/or methacrylated gelatin macromers, wherein the first natural polymer macromers are crosslinked with a first agent to form a first crosslinking network, and the second natural polymer macromer are crosslinked with a second agent different than the first agent to form a second crosslinking network, wherein the first agent crosslinks the first natural polymer macromers but not the second natural polymer macromers, and the second agent crosslinks the second natural polymer macromers but not the first natural polymer macromers, and wherein aldehyde groups of the oxidized acrylates form imine-bonds with amine groups of the acrylated and/or methacrylated gelatin macromers to form a third crosslinking network,
and wherein a plurality of cells are encapsulated within the hydrogel and mechanical stimulation of the hydrogel enhances cell proliferation and differentiation.

2. The composition of claim 1, wherein the elasticity of the hydrogel is substantially maintained during degradation.

3. The composition of claim 1, wherein the first natural polymer macromers are ionically crosslinkable with the first agent.

4. The composition of claim 1, wherein the second natural polymer macromers are photocrosslinkable with the second agent.

5. The composition of claim 1, further comprising at least one bioactive agent.

6. The composition of claim 1, wherein the cells comprise progenitor cells, undifferentiated cells and/or differentiated cells.

7. The composition of claim 6, wherein the cells include mesenchymal stem cells.

8. A composition comprising:
a triple-network hydrogel having three types of crosslinking networks that includes a crosslinked first natural polymer macromers with a first elasticity and a homogenously distributed interpenetrating network of crosslinked second natural polymer macromers having a second elasticity higher than the first elasticity, the triple-network hydrogel being cytocompatible, and, upon degradation, produce substantially non-toxic products, wherein the elasticity of the hydrogel is substantially maintained during degradation,
wherein the first polymer macromers are oxidized alginates and the second polymer macromers are acrylated and/or methacrylated gelatin macromers, wherein the first natural polymer macromers are crosslinked with a first agent to form a first crosslinking network and the second natural polymer macromer are crosslinked with a second agent different than the first agent to form a second crosslinking network, wherein the first agent crosslinks the first natural polymer macromers but not the second natural polymer macromers, and the second agent crosslinks the second natural polymer macromers but not the first natural polymer macromers, and wherein aldehyde groups of the oxidized acrylates form imine-bonds with amine groups of the acrylated and/or methacrylated gelatin macromers to form a third crosslinking network,
and wherein a plurality of cells are encapsulated within the hydrogel and mechanical stimulation of the hydrogel enhances cell proliferation and differentiation.

9. The composition of claim 8, wherein the first natural polymer macromers are ionically crosslinkable with the first agent.

10. The composition of claim 8, wherein the second natural polymer macromers are photocrosslinkable with the second agent.

11. The composition of claim 8, further comprising at least one bioactive agent.

* * * * *

UNITED STATES PATENT AND TRADEMARK OFFICE
CERTIFICATE OF CORRECTION

| | | |
|---|---|---|
| PATENT NO. | : 11,759,549 B2 | Page 1 of 1 |
| APPLICATION NO. | : 16/107708 | |
| DATED | : September 19, 2023 | |
| INVENTOR(S) | : Eben Alsberg | |

It is certified that error appears in the above-identified patent and that said Letters Patent is hereby corrected as shown below:

In the Specification

Column 1, Line 13, under the heading GOVERNMENT FUNDING, the following paragraph should read:
--This invention was made with government support under AR069564, CA108512, AR066193, and AR007505 awarded by the National Institutes of Health. The government has certain rights in the invention.--

Signed and Sealed this
Seventeenth Day of October, 2023

Katherine Kelly Vidal

Katherine Kelly Vidal
*Director of the United States Patent and Trademark Office*